(12) United States Patent
Brauss

(10) Patent No.: US 7,265,754 B2
(45) Date of Patent: Sep. 4, 2007

(54) METHOD FOR DISPLAYING MATERIAL CHARACTERISTIC INFORMATION

(75) Inventor: Michael Brauss, Amherstburg (CA)

(73) Assignee: Proto Manufacturing Ltd. (CA)

( * ) Notice: Subject to any disclaimer, the term of this patent is extended or adjusted under 35 U.S.C. 154(b) by 407 days.

(21) Appl. No.: 10/706,385

(22) Filed: Nov. 12, 2003

(65) Prior Publication Data
US 2005/0099423 A1    May 12, 2005

(51) Int. Cl.
*G06T 11/20* (2006.01)
*G01N 23/20* (2006.01)

(52) U.S. Cl. .......................... 345/440; 378/70; 378/72
(58) Field of Classification Search ................. 345/440
See application file for complete search history.

(56) References Cited

U.S. PATENT DOCUMENTS

| | | | |
|---|---|---|---|
| 4,812,976 A * | 3/1989 | Lundy ....................... 600/523 |
| 5,506,955 A * | 4/1996 | Chen et al. ................... 714/26 |
| 5,684,945 A * | 11/1997 | Chen et al. ................... 714/20 |
| 5,894,311 A * | 4/1999 | Jackson ....................... 345/440 |
| 5,895,439 A * | 4/1999 | Fisher et al. .................. 702/36 |
| 5,940,545 A * | 8/1999 | Kash et al. .................. 382/312 |
| 5,952,576 A * | 9/1999 | Schwarz ....................... 73/579 |
| 6,243,615 B1 * | 6/2001 | Neway et al. ............... 700/108 |
| 6,505,140 B1 * | 1/2003 | Bachrach .................... 702/166 |
| 6,721,393 B1 | 4/2004 | Brauss |
| 6,826,507 B2 * | 11/2004 | Kroboth et al. ............. 702/127 |
| 6,925,146 B2 | 8/2005 | Brauss |
| 2003/0031357 A1 * | 2/2003 | Wenzel et al. .............. 382/154 |
| 2003/0126054 A1 * | 7/2003 | Purcell ........................ 705/36 |
| 2003/0144868 A1 * | 7/2003 | MacIntyre et al. ............. 705/1 |
| 2003/0182069 A1 * | 9/2003 | Banes et al. .................. 702/33 |
| 2003/0208323 A1 * | 11/2003 | Hao et al. ..................... 702/41 |
| 2004/0073477 A1 * | 4/2004 | Heyns et al. ................. 705/10 |
| 2004/0179012 A1 * | 9/2004 | Ingber et al. ............... 345/440 |
| 2004/0260178 A1 * | 12/2004 | Kahn et al. .................. 600/437 |
| 2005/0035967 A1 * | 2/2005 | Joffrain et al. .............. 345/440 |
| 2005/0039170 A1 * | 2/2005 | Cifra et al. .................. 717/125 |
| 2005/0091012 A1 * | 4/2005 | Przytula et al. ................ 703/2 |
| 2005/0154563 A1 * | 7/2005 | Hassler et al. ............. 702/189 |
| 2005/0197806 A1 * | 9/2005 | Eryurek et al. ............. 702/188 |

\* cited by examiner

*Primary Examiner*—Ulka Chauhan
*Assistant Examiner*—Eric Woods
(74) *Attorney, Agent, or Firm*—Fitch, Even, Tabin & Flannery

(57) ABSTRACT

A system and method for displaying graphical information indicative of a plurality of material characteristics for a portion of a part under test. Energy is directed at the selected portion of the part under test. Resultant energy is detected from the selected portion of the part under test and data representative of each of a plurality of material characteristics for the portion of the part under test is obtained based, at least in part, upon the detected energy. A plurality of graphs is formed based upon the obtained data. Each of the graphs has information indicative of a separate one of the plurality of material characteristics. The plurality of graphs is displayed discrete from each other in a manner that facilitates substantially simultaneous visual comparisons between the information contained in each of the plurality of graphs.

22 Claims, 13 Drawing Sheets
(5 of 13 Drawing Sheet(s) Filed in Color)

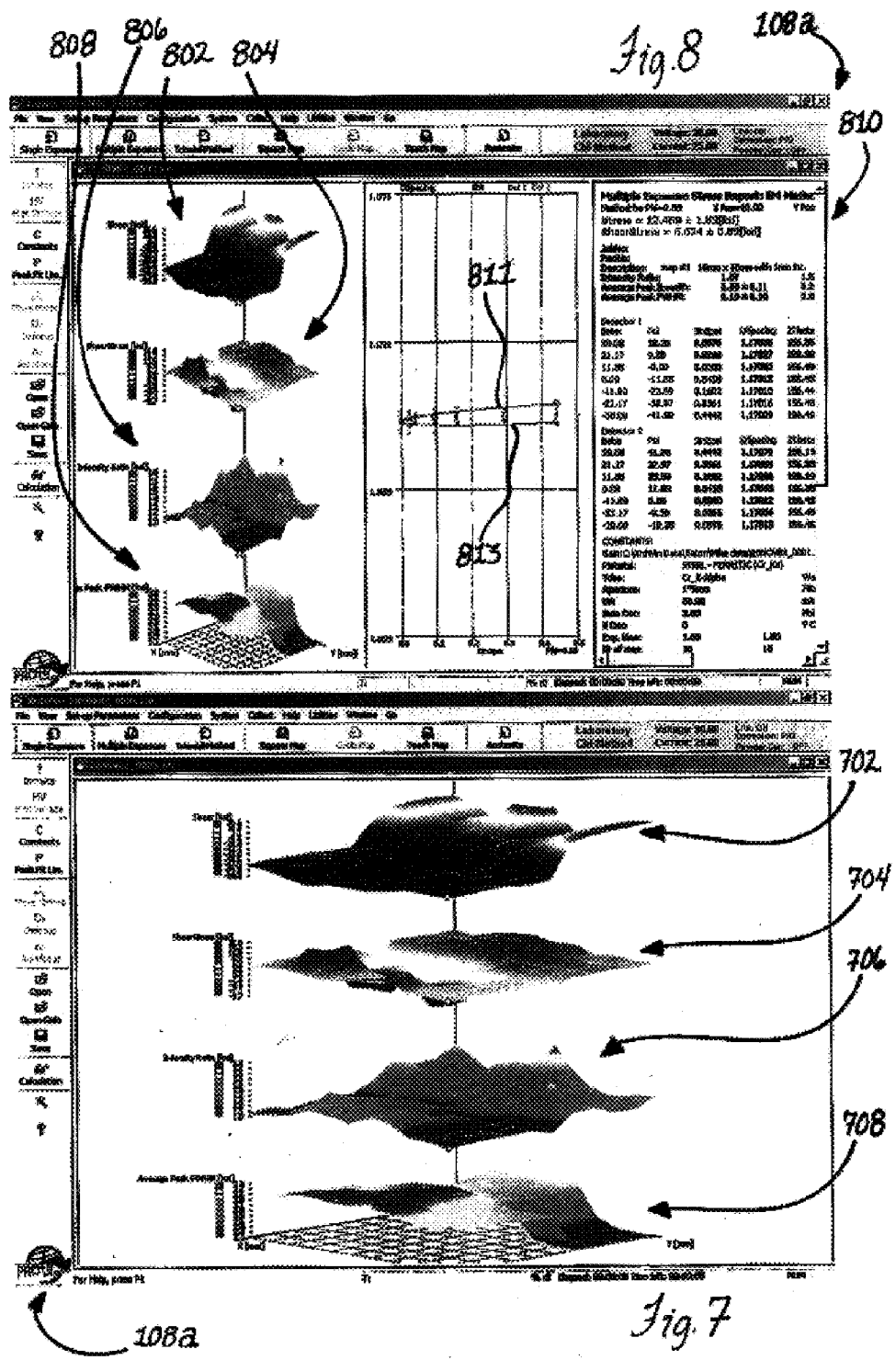

METHOD FOR DISPLAYING MATERIAL CHARACTERISTIC INFORMATION

FIELD OF THE INVENTION

The invention relates to systems and methods for displaying a plurality of material characteristics in a format that facilitates comparisons between the characteristics.

BACKGROUND OF THE INVENTION

The failure of fatigue-limited components in various types of systems often leads to undesirable or tragic consequences. For instance, the failure of a critical component of a jet engine during the operation of the engine may result in the loss of human life or other tragic results. Directed energy measurement techniques have been developed to test these critical components, detect defective components, and prevent undesirable situations from ever taking place.

Typically, directed energy measurement techniques involve directing energy at a part under test and sensing the resulting diffracted energy and/or attenuated energy. If a diffraction technique is used, the resulting sensed diffraction peak is interpreted to arrive at a measurement of a material characteristic. With energy attenuation techniques, the amount of energy that is absorbed by the material is determined and this amount is used to determine the same or additional types of material characteristics.

The material characteristics of the part under test often are related to stress. For example, stress may be determined along or under the surface of the part under test. Additionally, the error present in measuring stress (stress error) may be calculated. If multiple sensors are used to detect diffracted energy, the ratio of two stress measurements, as determined at the two different sensors (intensity ratio), can be determined.

Another characteristic that can be determined is the average peak breadth of the stress measurement. This is usually defined as the width of the Gausian distribution of stress as measured at a sensor. Average full width half magnitude (FWHM) (average full width at half maximum of the Gausian function for stress as measured at a sensor) may also be determined.

The shear stress can also be determined. Further, a stress tensor may be determined by taking multiple measurements of stress and determining the magnitude and direction of the stress in the part under test. An error tensor, relating to the magnitude and direction of error in the stress tensor, can also be calculated. Stress may also be determined as a function of position in the x-direction or as a function of position in the y-direction. The maximum stress in any direction (equivalent stress) may also be obtained. Other characteristics can also be determined.

After the material characteristics have been determined, it is often desirable to display this information to an operator of the measurement equipment. For instance, the values of these characteristics can be mapped into two or three-dimensional graphs and displayed to the operator using a video terminal. However, present systems and methods only display a graph relating to a single material characteristic of the part under test.

SUMMARY OF THE INVENTION

In accordance with the present invention, a method and system are provided that enable optimized part analysis based on several different measured characteristics of the part. In this regard, part testing is used to generate raw data from which measurement values are generated for the different characteristics of the part material with the measurement values for each characteristic graphed and displayed in a manner that facilitates ready comparisons between the information contained in the graphs. Thus, the same raw data is used to generate multiple graphs each directed to a different material characteristic for substantially simultaneous display. Preferably, the formatted outputs or graphs are all displayed on a single screen. This facilitates visual comparisons between the information displayed in the graphs of the different characteristics on the tested part material.

Thus, in the present method and system several different graphs will appear on one screen with each displaying variations in measurements for the material characteristics they map for the viewer. For example, a stress graph will appear adjacent a graph for retained austenite to show how these material characteristics fluctuate relative to each other. The graphs can be aligned with each other such as along an axis corresponding with the magnitude of the measured characteristic or along an axis (or axes for 3D graphs) corresponding to the region along the part that is tested. This allows an operator to easily make visual comparisons between the measured characteristics to determine where, for instance, potential or actual trouble spots exist in the tested region of the part.

In another aspect, the information provided in the graphs of the part material characteristics can be utilized to develop an evaluation guide or guides that coordinate or correlate the measurements relative to each other to inform an action that is to be taken on the part, such as for quality control or part maintenance purposes. The evaluation guide itself, when correlative of different measured part characteristics, can be graphed to allow an operator to see how close or far from the threshold for action the correlated measurements are. In this manner, an operator can primarily refer to the guide until the threshold is approached. At that, and with the proper notification, the operator can then check the material characteristic graphs that represent the characteristics on which the evaluation guide is based. This can indicate to the operator why the threshold for the guide is being approached providing the operator a useful evaluative tool to gain information regarding the condition of tested part material.

As has been mentioned, pursuant to the present invention and system, graphical information indicative of a plurality of material characteristics is displayed for a portion of a part under test. Energy is directed at the selected portion of the part under test. Resultant energy is detected from the selected portion of the part under test and data representative of each of several different material characteristics for the portion of the part under test is obtained based, at least in part, upon the detected energy. Different graphs can be simultaneously formed based upon the obtained data. Each of the graphs includes information indicative of a separate one of the material characteristics. The graphs are displayed discrete from each other in a manner that facilitates substantially simultaneous visual comparisons between the information contained in each of the graphs. To this end, it is preferred that the graphs all appear on a single screen such as aligned along a z-axis, which is the axis used to measure the magnitude of the tested characteristic, e.g. stress or retained austenite levels in part material.

The present condition of a given part under test cannot always be adequately determined by current systems, which examine only a single characteristic such as any of those noted above. Instead, a test operator will typically wish or otherwise have need to access a plurality of different characteristics for a given part under test. In current systems, a three-dimensional graph indicating stress values may be displayed. An operator desiring to view multiple characteristics, however, must alternate generating and then viewing the different graphs of the different characteristics. In other words, an operator has to view a screen showing one graph, and then replace the graph with another graph that is generated then displayed on the screen, thereby having to recall what they previously viewed. This display and comparison technique is cumbersome and time consuming to accomplish and comparisons between different characteristics are often difficult or impossible to make.

Accordingly, multiple graphs of multiple material characteristics for a part under test may be displayed in a manner that facilitates comparisons between the different material characteristics. The graphs are preferably displayed on a single screen are aligned along a common axis. Aligning along a common axis, for example, the z-axis, allows a viewer to easily compare the characteristics of two or more material characteristics. Within the region tested, the viewer can easily determine if one of the material characteristics has suspicious values, and readily compare that graph to the graphs relating to other characteristics to see if the values of the other material characteristics also have suspect values in the tested region, for instance.

To further facilitate comparisons, the viewer can vary the scale of the z-axis in the three-dimensional graphs thereby customizing the resolution of the displayed characteristics. Fine tuning the resolution for each of the graphs independent of the others is advantageous since a scale that adequately displays one characteristic may be unsuitable to display another characteristic. Hence, a viewer can readily program the scales to clearly see distinctions in the characteristics and is not confined to any single, preprogramed scale for any of the graphs.

The viewer can use other techniques to aid visual comparisons between the graphs. For example, the viewer can change the color of the graphs, overlap graphs, and customize the fill characteristics of the graphs. All of these parameters may be varied so that the visual display emphasizes distinctions and/or potential trouble areas of the part under test.

If the viewer needs further aid in determining the viability of a part, they may generate a report for a particular location on the part under test. In one example, the report indicates the exact measurement values of a location on the part under test. Conveniently, the report can be generated by having the user click on the point on the screen corresponding to the part location where the viewer wants to generate the report. Reports are particularly useful, because, in some instances, the viewer may not be able to visually discern values on the graph or may otherwise need to determine more exact values that are readily visible.

As has been mentioned previously, pursuant to one aspect of the present invention, an evaluation guide or guides is determined. An evaluation guide defines a relationship between two or more material characteristics for the part under test, for instance, between stress and strain. A set of guide values (e.g., (GSTRESS1, GSTRAIN1); (GSTRESS2, GSTRAIN2), etc.) is formed when guide values for a first material characteristic values are applied to the guide, and the evaluation guide is used to determine the remaining guide values associated with the other material characteristics. In a specific example, if the guide specifies a linear relationship between stress and strain (e.g., strain=stress), then the guide values of (1,1); (2,2); and so forth may be determined.

As stated above, raw data is received from sensors as x-ray diffraction information. This raw data, including intensity readings for a given diffraction angles, is used to calculate measurement values, which specify the magnitude of a particular material characteristic at a particular point on the part under test. Preferably, the measurement values for multiple characteristics are formed simultaneously or substantially simultaneously. In the present example, raw data is received and converted into measurement values for stress and strain.

Comparisons may be made between the guide values associated with the guide and the actual measurement values associated with the material characteristics of the guide. Specifically, after an evaluation guide and guide values are determined, test measurement resultants are formed from the sets of measurement values for the same material characteristics associated with the evaluation guide. Each test measurement resultant includes two or more measurement values relating to the material characteristics in the evaluation guide at a particular point on the part under test. After the test measurement resultants are formed, the test measurement resultants are compared to the guide values. In the present example, measurement values for stress (e.g., (STRESS1, STRESS2, etc.) and strain (STRAIN1, STRAIN2, etc.) are formed into test measurement resultants (TSTRESS1, TSTRAIN1), (TRSTESS2, TSTRAIN2), and so forth.

Different types of comparisons between the guide values and the test measurement resultants may be made. In one approach, the guide values may be plotted on a graph and the test measurement resultants also plotted on the same graph. Then, a zone may be defined as an area about the guide values where the test measurement resultants are expected to fall. If the test measurement resultants fall outside of the zone, an action can be taken by the viewer. Plotting the guide values and the test measurement resultants offers a convenient and easy way for the operator to make a determination that the part is potentially defective.

In the present example, after an evaluation guide and guide values relating stress to strain are determined and plotted as a line on a graph, a zone can be defined about the line. Then, the test measurement resultants ((TSTRESS1, TSTRAIN1); (TRSTESS2, TSTRAIN2), etc.) may be plotted on the same graph. A comparison is made to see if the test measurement resultants fall within the zone or outside the zone. If a test measurement resultant falls outside of the zone, the operator may make a determination that further action should be taken.

In other examples of comparisons using an evaluation guide, the guide values can define a threshold, which can be compared to the test measurement resultants. The guide values may represent a ceiling under which all test measurement resultants should be below or a floor over which all test measurement resultants should be above. The guide values can be graphed and the test measurement resultants plotted against the guide values on the same graph. Easy comparisons between the location of the test measurement resultants relative to the guide values can be made. In the current example, the test measurement resultants (e.g., (TSTRESS1, TSTRAIN1); (TSTRESS2, TSTRAIN2), etc.) may be plotted and compared to the guide values (e.g., (GSTRESS1, GSTRAIN1); (GSTRESS2,GSTRAIN2, etc.).

In still another approach, a first threshold value for a material characteristic may be defined. For example, a threshold value of 10 ksi may be determined for stress. Based upon this threshold, a second threshold value relating to a second material characteristic may be determined based upon a relationship, for example, an equation or set of equations that relate the material characteristics. For instance, if stress and strain are related by a linear relationship (e.g., strain=stress), then the second threshold for strain would also be 10 ksi.

After the thresholds are determined, selected measurement values for the selected characteristics (e.g., stress and strain) are monitored in real time as the measurement values are calculated from the raw data. They can be monitored at a particular point or points on the part under test. In one example, if the measurement values exceed one or more of the thresholds, the operator may be alerted and an action may be taken by the operator. In another example, the measurement values are monitored and when these values approach to within a certain limit of any or all of the thresholds, the operator is alerted and an action may be taken. This approach offers a convenient and automatic way for thresholds and limits to be set by an operator and defective parts detected. Advantageously, the operator does not have to constantly examine the graphs to determine if a threshold is exceeded or manually calculate multiple threshold values.

In another preferred embodiment, a system is provided for displaying graphical information indicative of different material characteristics for a portion of a part under test. The system includes an energy emitter. The emitter directs energy at a selected portion of a part under test. The system also includes an energy detector that detects resultant energy from the selected portion of the part under test. The detected energy is transmitted to a controller either already processed into measurement data or for processing it into data for the different material characteristics being tested. The data can be stored in memory. The controller is coupled to the memory and includes an output coupled to the display for generating graphs of the measurements for each of the tested material characteristics of the part.

Preferably, the controller generates the graphs on a single screen in order to facilitate visual comparisons between the measured material characteristics. For example, the visual comparisons can determine where measurements are relatively high or low as compared to other measurements relating to characteristics of the part material. If this determination is made, the user make take further appropriate action as may be deemed necessary. In another form, the controller may generate an evaluation guide based upon a predetermined relationship between at least two of the measured material characteristics. As previously mentioned, the controller may graph the guide values and plot test measurement resultants against the guide. A zone may then be identified about the guide to define a region about the guide where test measurement resultants may fall and still be deemed acceptable. The viewer can then visually determine whether the test measurement resultants fall within the zone, above the evaluation guide, or below the evaluation guide. In other words, the viewer can visibly determine whether deviations of the measurement values represented in the test measurement resultant from the evaluation guide are acceptable based upon whether the test measurement resultants fall within or out of the zone.

Based upon the visual review of the graphs, the operator may take actions. By displaying the graphs of material characteristics on a single screen, potential problems of a part under test can be easily detected and corrective action taken before the part fails, for instance. This can be extremely important in applications such as aircraft engines where a failure can cause catastrophic results. The operator may pull the part to be tested, perform further tests on the part, alert others that the part is suspicious, and record the identity of the part for future reference.

The evaluation guide is also beneficial because a viewer can easily determine how test measurement resultants compare against the evaluation guide. Again, this determination can easily be made and corrective action quickly taken before the part under test fails. In this regard, and as has been discussed above, the operator can view the evaluation guide in graphical form and compare the guide to test measurement resultants as the measurement values are taken. If the comparison between the guide and the values indicates nonconformance, then the operator can take appropriate action.

The embodiments are useful to effect various economical, reliable, relatively intuitive, and relatively scalable solutions to at least some of the various concerns and issues noted herein.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

FIG. 7 is a view of a single screen display of the system of FIG. 1 showing stress, shear stress intensity ratio and average peak FWHM aligned along a common axis;

FIG. 8 is another single screen display showing stress, shear stress, intensity ratio and average peak FWHM aligned along a common axis along with a report of characteristics at a point of the part under test;

Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present invention. Also, common but well-understood elements that are useful or necessary in a commercially feasible embodiment are typically not depicted in order to facilitate a less obstructed view of these various embodiments of the present invention.

DETAILED DESCRIPTION OF THE PREFERRED EMBODIMENTS

Figure 1:
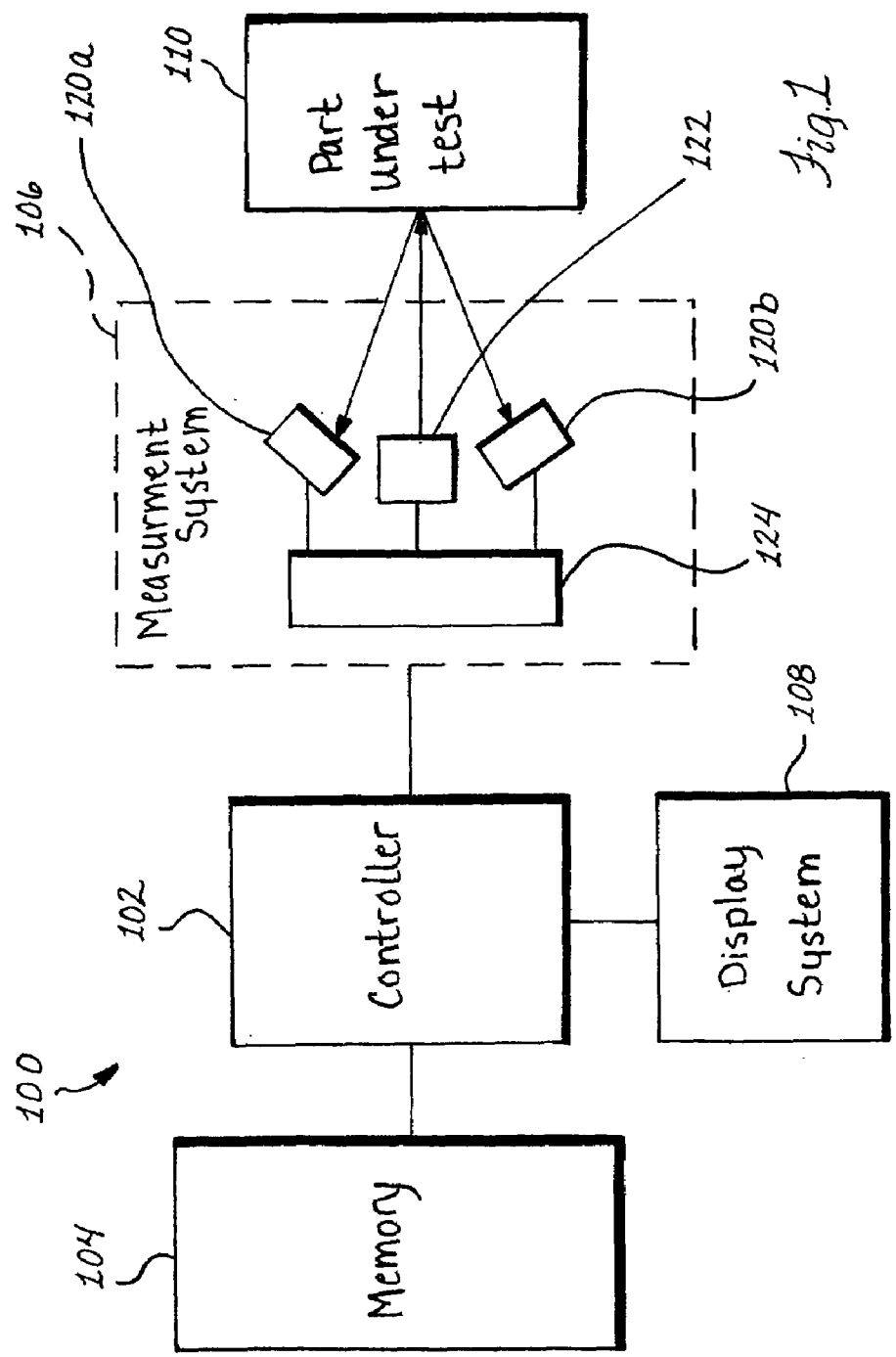
FIG. 1 is a block diagram of a system for displaying graphical information by directing x-rays to a part under test in accordance with a preferred embodiment of the present invention.

Referring initially to FIG. 1, a system 100 for graphically displaying energy measurement information for a part under test 110 preferably includes a controller 102, a memory 104, a measurement system 106 and a display system 108. The controller 102 is communicatively coupled to the memory 104, the measurement system 106, and the display system 108. The measurement system 106 preferably includes an energy emitter 122, energy detectors 120a and 120b, and a control module 124. As will be explained in greater detail below, the emitter 122, under the control of the control module 124, directs energy to the part under test 110, and the detectors 120a and 120b detect resultant energy from the part under test 110. The directed energy may include any form of energy, for instance, x-rays or thermal energy. The resultant energy detected by the detectors 120a and 120b may be diffracted energy or attenuated energy. Other forms of directed and resultant energy are possible. In accordance with the preferred form of the invention, raw data is obtained from the detected energy which is then used as the common data to generate several measurements each of a different material characteristic of the part, e.g., stress, retained austenite, and grain size, as will be described further hereinafter.

The part under test 110 is often a component of a high-performance system where a failure of the part may result in tragic consequences. For example, the part under test 110 may be an aircraft engine component where a failure of the component may result in the loss of the engine and aircraft. Thus, it is important to be able to determine the reliability of parts in the system and, specifically, to determine the unreliability of a part before the part actually fails.

Most often, the determination of the reliability of the part under test 110 is made based upon measuring multiple material characteristics of the part under test 110. For example, the stress in a particular point may be measured as well as the retained austenite value for that point. Particular values of stress together with particular values of retained austenite may indicate the unreliability of the part under test 110. However, with current systems the information regarding one particular part material characteristic is only generated at any one time and displayed on a screen. In other words, if the operator needs to compare two or more material characteristics of the part under test 110, they would have to view the information on separate video terminals. Alternatively, the operator must remember the information concerning the first material characteristic and then generate the information for a second material characteristic for display on the screen showing only this information concerning the second material characteristic in an attempt to make a comparison between the two material characteristics. Obviously, both approaches are cumbersome and inconvenient for the operator.

In the present system, information regarding several tested material characteristics of the part under test 110 can be displayed on the same screen 108a of the display system 108. Specifically, an operator can view the screen 108a and simultaneously have generated and displayed to them measurement information regarding several different material characteristics for the part under test 110. The simultaneous display of the information on a single screen 108a allows the operator to readily check measurements for different material characteristics without having to take further intervention or needing additional computer hardware such as another screen or the like for this purpose. In addition, the same data can be used to develop the displayed graphs so that additional testing need not take place for comparison purposes. Preferably, the information in the graphs is arranged in a manner that leads an operator to make easy comparisons between the information such as by aligning the graphs along the z-axis as will be described further hereafter.

Based upon viewing the characteristics together, the operator can visually determine that some values are high relative to other values and some values are low relative to other values. The high and low values may exceed acceptable limits for the material characteristic. Since the graphs are displayed together, the operator can make fast and easy comparisons of the material characteristics to determine, based upon all or some of the characteristics displayed, and determine whether an action needs to be taken regarding the part under test 110.

Figure 11:
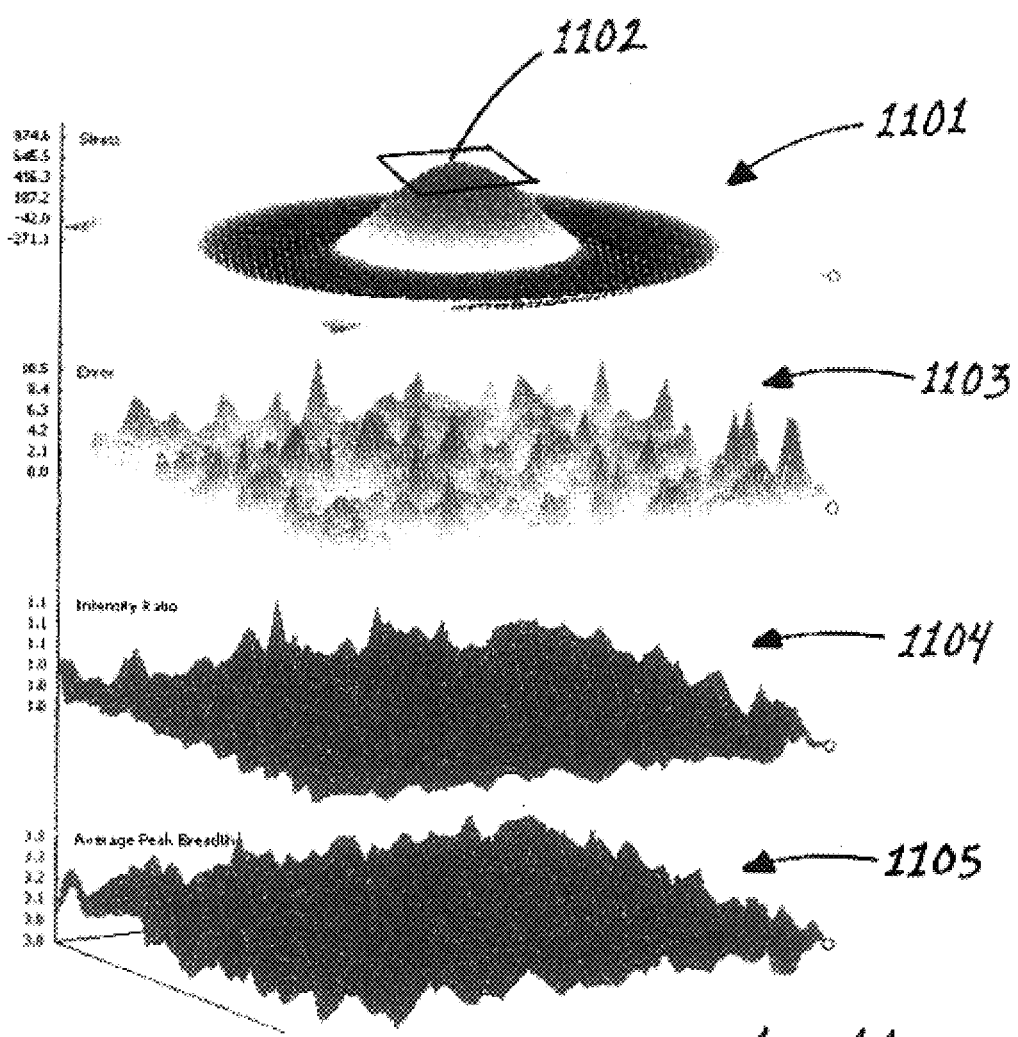
FIG. 11 is a single screen display of graphs showing stress, error, intensity ratio and average peak breath aligned along a common axis.

In one example, and referencing FIG. 11, graphs 1101, 1103, 1104, and 1105 showing the stress, error, intensity ratio, and peak breath are displayed on top of each other along the z-axis on the single screen 108a. An examination of the stress graph 1101 indicates that stress reaches a maximum value in an area 1102. As can also be seen, the values of the other material characteristics vary over the tested area of the part under test 110 and also within the corresponding area 1102 in their graphs. This may indicate that the part under test 110 may be defective requiring that further action concerning the part under test 110 should be taken.

The operator, after viewing the graphs on the screen 108a, may take an action as a result of the viewing. For instance, if the operator views the graphs and recognizes that the combination of displayed characteristics represents a problematic location on the part, then the part can be pulled. In another example, if the viewing indicates that the part may have problems, further testing may be performed on the part. As is apparent, the operator can conveniently make this determination after viewing the graphs on a single screen. In the example of FIG. 11, the viewer may notice that stress reaches an extremely high value in the area 1102 on the graph 1101 and pull this part for further testing. On the other hand, the fact that none of the graphs 1103–1105 show a similar concentration of high values may indicate that the point is still within safe and tolerable levels for the various characteristics tested.

Besides graphs, reports and other types of information may be displayed on the single screen 108a. Specifically, a report indicating additional information concerning a point or location on the part under test may be generated and displayed alongside the graphs. The report indicates exact value measurements for a specific point. For example, a report for a point may indicate stress, shear stress, and retain austenite values for the point in question. Displaying a report is useful in many situations because a user may want to see exact measurement values or other information about a measured point in a discrete format alongside the visual format of the graphs. In some instances, the graphs may be difficult to read and in other instances, the viewer may need to know an exact value, for instance, if the measurement value on the corresponding graph appears to border on being unacceptable.

Figure 10:
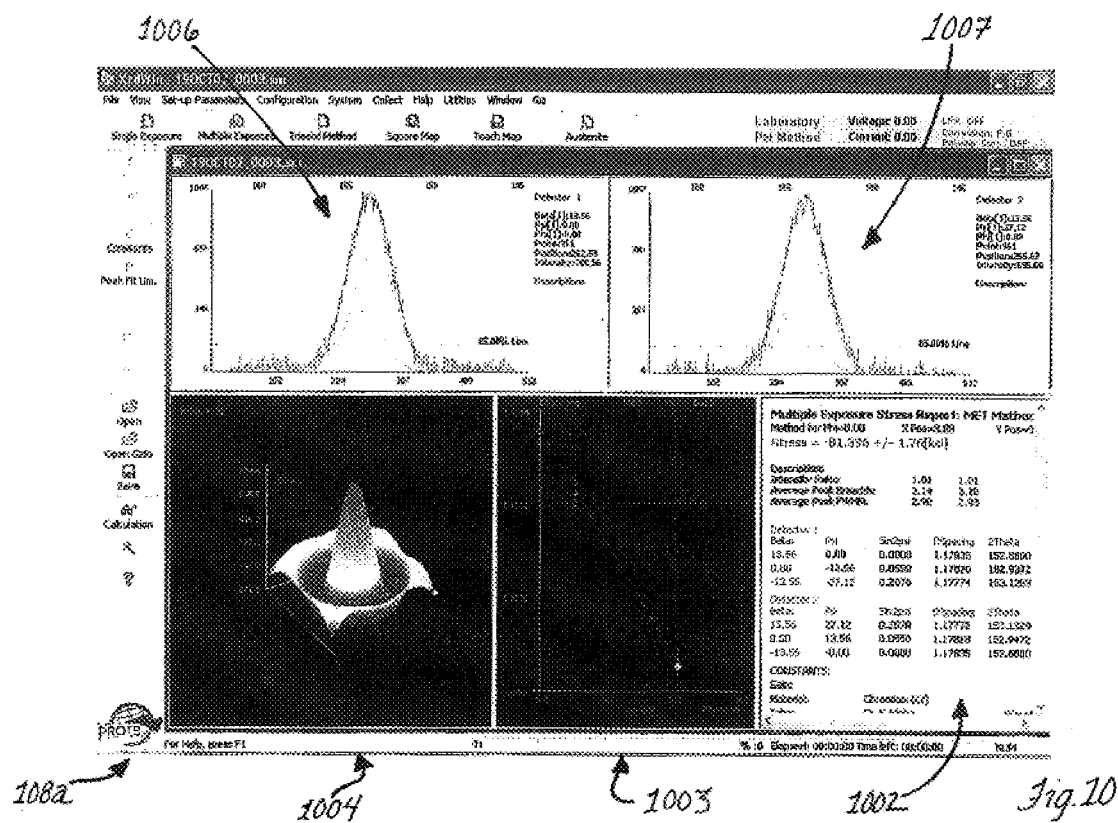
FIG. 10 is a single screen display showing two and three dimensional graphs of tested material characteristics and a report based thereon.

Referring now to FIG. 10, a report 1002 is shown alongside a graph 1004. The report 1004 shows the measured stress, intensity ratio, average peak breath, and average peak FWHM for a particular point on the part under test 110 as measured from two detectors. Also, the stress for the selected point is −81.336 ksi. In one example of use of this report, the operator may know that values of stress less than −81 ksi indicate that the part needs to be pulled. However, looking at the graph 1004, it is difficult to determine if this threshold has been exceeded. However, by clicking on the point to be examined using a computer mouse, the report 1002 is generated and the operator can readily see the stress value, determine the value exceeds the threshold, and pull the part under test 110 for further testing.

Another benefit of the present system is that an evaluation guide or guides may be determined. The evaluation guide may be determined by the operator to indicate a relationship between two or more material characteristics. Based upon the evaluation guides, guide values may be calculated and displayed upon the single screen 108a. In addition, test measurement resultants may be determined. The test measurement resultants include two or more measurement values for a particular point on the part under test for the same material characteristics defined in the guide. For instance, if the guide relates stress to strain, test measurement resultants are formed from measurement values of stress and strain with each test measurement relating to a point on the part under test.

Since the test measurement resultants include measurement values associated with the same material characteristics of the guide, the test measurement resultants can be plotted on the same graph as the guide values and compared to the guide values. In addition, the guide values and test measurement resultants may be displayed alone on the single screen 108a or together with the graphs of the material characteristics of the part under test 110.

Figure 14:
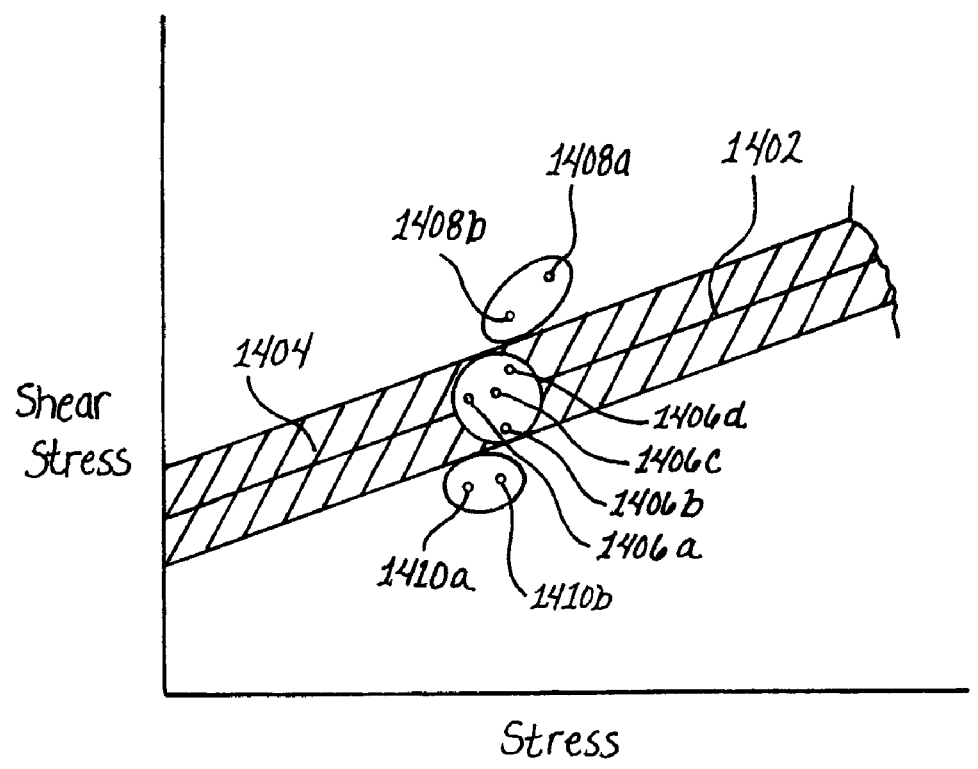
FIG. 14 is a graph of an evaluation guide and plotted measurement values.

In one example of the use of the evaluation guide, and referring now also to FIG. 14, guide values for an evaluation guide are plotted as the guide line 1402. As can be seen, the relationship indicated by the guide values of the guide line 1402 is linear. In this case, the relationship defined by the guide line 1402 is a target value that relates how the two material characteristics should ideally compare. A zone 1404 is also identified about the line 1402 that defines an acceptable extent of deviation from the guide line 1402.

Test measurement resultants 1406a–d, 1408a–b, and 1410a–b are formed from the measurement values relating to the particular material characteristics of the evaluation guide and are plotted. An operator can view the graph and see that the group of plotted test measurement resultants 1406a–d fall within the zone 1404, indicating that the measurement values represented by these test measurement resultants 1406a–d are acceptable. However, the test measurement resultants 1408a–b and 1410a–b do not fall within the zone 1404, indicating that for some points on the part under test 110, the measurement values are not acceptable. Once the operator sees that a test measurement resultant falls outside of the zone 1401, the operator may take an action, for example, removing the part under test for further testing or investigate which of the material characteristics is suspect. Thus, the evaluation guide offers an alternate and convenient way to determine whether measurement values fall within acceptable limits.

Alternatively, the evaluation guide may be used as a threshold. In the case of the evaluation guide depicted in FIG. 14, the guide line 1402 could represent a threshold. This threshold may be a ceiling in which all measurement values were not to exceed or a floor that measurement values were not to fall below. If the guide line 1402 were an upper threshold, then it can be seen that the test measurement resultants 1408a–b a, 1406a, 1406c, and 1406d fall above the threshold. Conversely, if the guide line 1402 represented a floor, then it can be seen that the measurement values in the test measurement resultant 1410a–b and 1406b fall below the guide line 1402. In either case, a viewer can readily determine if the threshold is exceeded and determine whether an action need be taken since, by exceeding a threshold, it is indicated that some measurement values are non-conforming.

In another approach, the viewer may determine that any test measurement resultant that exceeds the threshold is still close enough to the guide line 1402 that no action need be taken. In this regard, the zone 1404 may be used as a visual aid to make this determination. Specifically, test measurement resultants that exceed the threshold but fall within the zone would still be considered acceptable. Alternatively, the viewer may determine that all test measurement resultants that are that beyond the threshold require an action to be taken. Thus, the user can readily determine if measurement values associated with the test measurement resultants meet a threshold so that an appropriate action may be taken.

The system may also keep track of how the test measurement resultants relate to the evaluation guide. In one example, the system may determine when the test measurement resultant approaches within a certain distance of the evaluation guide in order to issue an alert when this occurs. In another example, the system may determine when the test measurement resultants leave the zone 1404 and alert the operator when this occurs.

The controller 102 may be any processor that is capable of executing computer instructions stored in a memory. For example, the controller 102 may be a microprocessor or the like. As shown in FIG. 1, the controller 102 and the control module 124 within the measurement system 106 may be separate devices. However, the controller 102 and the control module 124 may also be included within the same device, for example, within the same microprocessor. In addition, the controller 102, memory 104, and display system 108 may be included within the same system component or housing, for instance, within a personal computer or contained on the same control board.

The controller 102 may receive raw data from the measurement system 106 and store the data in the memory 104. The data may be stored in an appropriate format and with other information, for example, headers, sufficient to identify the data and allow the information to be retrieved from the memory 104 by the controller 102. The controller 102 may also receive and store the evaluation guides in the memory 104.

The controller 102 simultaneously determines the material characteristics from the diffraction data received. Specifically, the controller 102 receives data indicating the intensity of the received energy for various diffraction angles. The controller 102 processes this data using various mathematical or calculus operations to obtain the measurement values for material characteristics. These operations can be performed substantially simultaneously by the programmed software of the controller 102 from a user perspective, although system resources may dictate that sequential rather than parallel processing of the algorithms occur. In one example of the operations the controller 102 performs, the controller 102 relates the intensities of the received energy to the corresponding diffraction angles and, from this relationship, determines the peak width. The controller 102 then uses the peak width to calculate the density, hardness, and grain size. In another example, the controller 102 determines the absolute peak value for the intensity of the received energy and uses the peak value to calculate strain.

The controller 102 may also, for example, extract previously processed information from the memory 104 as requested by an operator at the display system 108 and process this information into a format that allows the information to be displayed via the display system 108 to the operator. For example, an operator at the display system 108 may require that a preexisting graph be retrieved from the memory 104 and displayed at the display system 108.

The controller 102 may also display the data on the display system in real time, as the data is received from the measurement system 106. An operator at the display system space may additionally request that specific types of measurements be made of the part under test 110. The operator can also request that certain numbers, types, and graphical formats of information be displayed. The controller 102 may receive and process other types of requests from the measurement system, as well.

The memory 104 may be any type of device that is capable of storing information. For example, the memory 104 may be a database where data of any type is stored. Other examples of memories are possible.

The memory 104 may store the data obtained from the measurement system 106. The storage format may follow any number of structures. For example, information relating to a particular characteristic of a particular part under test may be stored in a single document or file. This document or file includes sufficient information for the controller 102 to identify and retrieve a particular document or file.

The measurement system 106 may be any type of system that is capable of directing energy at a part under test 110 and detecting resultant energy from the part under test 110. As shown in FIG. 1, the measurement system 106 preferably includes the energy emitter 122, energy detectors 120*a* and 120*b*, and the control module 124. The energy emitter 122 may direct energy, for instance, x-rays or thermal energy, onto the part under test 110. Resultant energy, for example, diffracted x-rays or attenuated energy, may be detected by the sensors 120*a* and 120*b*.

Although only a single emitter and two sensors are shown, it will be understood by those skilled in the art that any number of emitters and sensors may be used. It will also be understood that the measurement system 106 may be stationary or it may mobile. In one example, the measurement system may be of the type described in co-pending application Ser. No. 09/539,346, "X-Ray Diffraction Apparatus and Method," now U.S. Pat. No. 6,721,393, which is incorporated herein by reference in its entirety. In another example, the measurement system may be of the type described in co-pending application Ser. No. 10/390,479 "X-ray Diffraction System and Method," now U.S. Pat. No. 6,925,146, which is incorporated herein by reference in its entirety.

The control module 124 within the measurement system 106 may control the movement and operation of the sensors 120*a* and 120*b* as well as the emitter 122. Specifically, the control module may move measurement system 106 across the part under test 110 in order to take measurements. In one example, this movement may be along the path of an arc. The control module 124 may also receive the information obtained at the sensors and forward the information to the controller 102 or the memory 104.

As previously discussed, the display system 108 is a video display system comprised of a single video screen 108*a*. The display system 108 allows an operator to request and display information stored in the memory 104 or initiate the measurement and display of information using the measurement system 106.

In one example of the operation of the system of FIG. 1, energy, for example, x-rays, may be directed from the emitter 122 of the measurement system 106 onto a portion of the part of under test 110. An operator may select the portion of the part of under test 110 where the energy is to be directed. The measurement system 106 may be move across the part under test 110, for instance, in an arc, to allow measurements to occur at various points in the path. The sensors 120*a* and 120*b* of the measurement system 106 detect the resultant energy, for example, diffracted x-rays or attenuated energy, from the part under test 110 and convert it into data in a format and form suitable for use by the controller 124. This data is forwarded to the controller 124, which then sends it to the controller 102. The controller 102 formats the raw data and places it into the memory 104. For example, the data may be identified in the memory 104 by its source, the identity of the part under test, or the location of the region of the part that was bombarded by the energy.

As previously described, the raw diffraction data received by the controller 102 may be analyzed according to various mathematical or calculus operations to simultaneously determine the material characteristics. The analysis is made by analyzing aspects of the relationship between the intensity of the received energy to the diffraction angle of the received energy. This information may also be displayed to an operator. For instance, the graphs 1006 and 1007 shown in FIG. 10 display the intensity of the received energy versus diffraction angle of the received energy as received at two sensors. The operator may use these graphs to visually determine whether the received information is the same or similar at both sensors. If graphs are radically different, it may indicate that a problem exists with the part under test or the sensors.

The display system 108 displays the graphs on a single screen 108*a*. The graphs may be aligned along a common z-axis, as shown, for example, in FIG. 11. Aligning the graphs along the common z-axis is beneficial because it allows the operator to make easy visual comparisons for measurement values for a particular area of the part under test 110. Further, the operator does not have to switch back and forth between viewing the graphs of different material characteristics and does not have to obtain two video terminals to view the graphs simultaneously. Instead, the viewer merely needs to examine the graphs as they are simultaneously displayed on the screen 108*a*. Thus, the view can make ready comparisons and determine if and when further action regarding the part under test needs to be taken.

In addition, the display system 108 may graphically depict evaluation guides and graph sets of measurement values against these guides, for example, as shown in FIG. 14. If the evaluation guide represents a target value, the viewer can determine whether the measurement values fall within an acceptable range of the guide. If the evaluation guide represents a threshold, then the viewer can determine whether the measurement values fall above or below the threshold. Once this determination is made, the viewer can determine whether or not to take any further action.

Conveniently, the operator may change the parameters for the display of the graphs on the screen 108a to make the viewing of the graphs easier. For instance, in order that the material characteristic may be displayed to show distinctions and differences in the measured values, the resolution (affecting the z-axis of the graph) may be modified.

In another example, the color of the graphs may be varied so that certain graphs or portions of graphs are prominent. This is useful in situations where some material characteristics are more important than other. The operator also can customize the resolution and dimensions of each graph. Detailed reports concerning the characteristics of a particular point on a graph may be generated, for example, by the operator selecting and clicking on a point on the graph using a computer mouse or other cursor control device.

To aid in distinguishing variations in the graphs and generally presenting the graphs in a visually pleasing format, various different display techniques may be employed. For instance, the three-dimensional graphs can be color-coded, with particular measurement ranges having a specific color. These colors may be customized for each graph by the operator. The three-dimensional graphs can also be filled with any type of graphical filling, for example, wire-frame, filled surface, or points. Further, an isobar projection of each graph may be created and displayed. Two-dimensional sectional planes can also be created and positioned within the three-dimensional graphs. The two-dimensional planes can be separately displayed as two-dimensional graphs. In addition, the operator may click and drag any section plane to dynamically update the two-dimensional graph corresponding to the section plane. Further, graphs can be overlapped with each other with different graphs having different colors.

Measurements may be made and graphs derived of the characteristics on the surface of the part under test 110. Alternatively, measurements may be made and graphs derived of the characteristics for points or areas underneath the surface of the part under test 110. In this case, the operator may select the location of the point or area. Further, measurements may be made and graphs derived for multiple points and/or locations. At the display system 108, graphs showing the characteristics may be shown along with graphs showing the characteristics at a particular depth or at a variety of depths.

Conveniently, the operator may also choose to display and/or monitor some or all of the graphs in real-time and take appropriate actions when thresholds are reached in the graphs. In addition, the display system may graph the evaluation guides and determine whether measurement values fall within certain distances of the evaluation guides. For instance, and referring again to FIG. 14, the display system may determine how far the test measurement resultants 1406a–d, 1408a–b, and 1410a–b are from the line 1402 or whether these resultants fall within the zone 1404. Based upon this determination, the system may alert an operator to take appropriate action.

Figure 2:
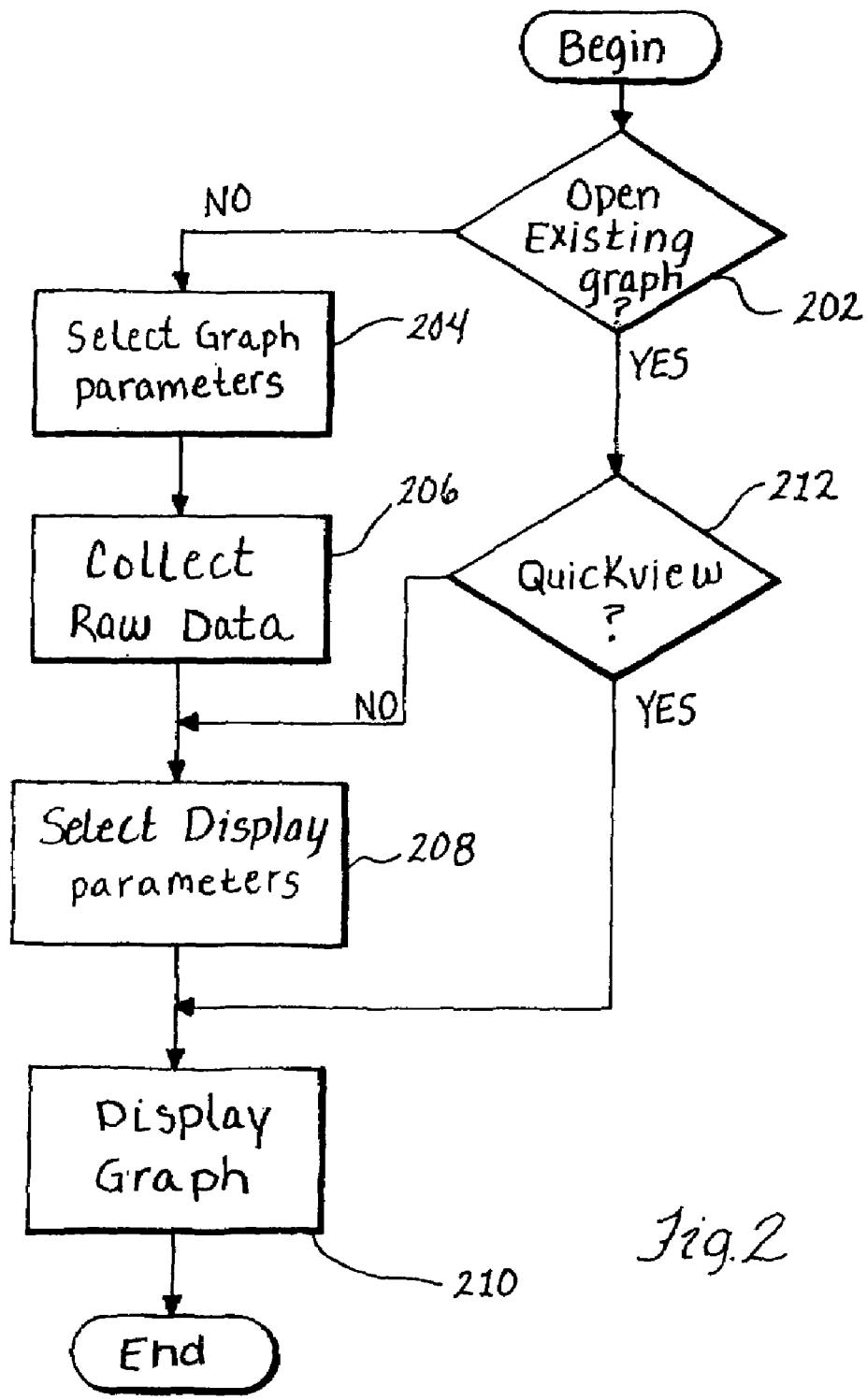
FIG. 2 is flowchart of a method for displaying graphical information to a user in accordance with another preferred embodiment of the invention.

Referring now to FIG. 2, one example of a corresponding method is described. At step 202, it may be determined whether it is desired to open an existing graph that already is stored in a memory. For example, a previously-generated graph may be stored in memory, and the operator may wish to view the graph to review the material characteristic indicated in the graph. As is known in the art, the graph may be stored in a computer file or similar arrangement. If the answer at step 202 is negative, then execution continues at step 204. If the answer at step 202 is affirmative, then execution continues at step 212.

At step 204, the operator can select parameters for the graph that the operator wishes to display. As will be explained in greater detail with respect to FIG. 3, this selection may include the type of graph to display, the size of the graph, and the resolution of the graph.

This step may include the acquisition of data for relating to the surface contours (the z-position of the portion of the part under test) for the portion of the part under test. In other words, a graph or mapping that depicts the shape or configurations of the region or portion of the surface of the part under test may be undertaken. Obtaining data indicating the z-position coordinates of the surface of the part under test may be desirable so that, for example, an energy emitter and/or sensor may be moved to a precise position above the part under test to properly focus directed energy at the part under test when measurements are conducted. One example of a method used to accomplish this mapping is described in copending application Ser. No. 09/539,346, "X-Ray Diffraction Apparatus and Method," which has been incorporated herein by reference in its entirety.

At step 206, data may be collected, for example, via the measurement system 106 in FIG. 1. In the example system of FIG. 1, the data may be transmitted from the measurement system 106 and stored in the memory 104 by the controller 102.

At step 208, the operator may select the parameters of the display. As will be discussed more fully with respect to FIG. 4, this may include determining the number of graphs to display, the layout of the graphs, the filling of the graphs, and the selection of particular areas of interest within the graphs to view.

At step 210, the graph can be displayed. For example, the graph may be displayed according to the graph parameters selected at step 204 and in accordance with the display parameters selected at step 208. The graph may be displayed on a video terminal or the like. The graph may be displayed using other display media, as well.

Suitable processing techniques such as of the Single Exposure Technique (SET), Linear technique, elliptical technique, or triaxial technique, may be used to process the data for each point of the graph into an intermediate form. Then, the intermediate form can be converted into a graph for display on the screen. The software may also establish reports and other types of information to be displayed on the screen using. For example, and now referring to FIG. 10, a report 1002 may be generated showing the measured stress, intensity ratio, average peak breath, and average peak FWHM for a particular point on the part under test 110 as measured from two detectors with all this information obtained from the same raw data.

The graph may also be an existing graph stored in a memory. In this situation, an operator may specify the identity of the graph to the controller, and, using this information, the controller may locate the graph in memory, retrieve the graph, and display the graph on a display system. Alternatively, if the graph is to be displayed in real-time, a controller may process the data into a graphical format and display the graph directly on the screen to an operator without first having to store the graph in memory. Periodic updates of the graph may also be made (for example, on an automatic basis or when initiated by an operator).

At step 212, it may be determined whether the operator wishes to view an existing graph quickly without, for example, having to set display parameters. If the answer is affirmative, then execution continues at step 210. If the answer is negative, then execution continues at step 208.

Figure 3:
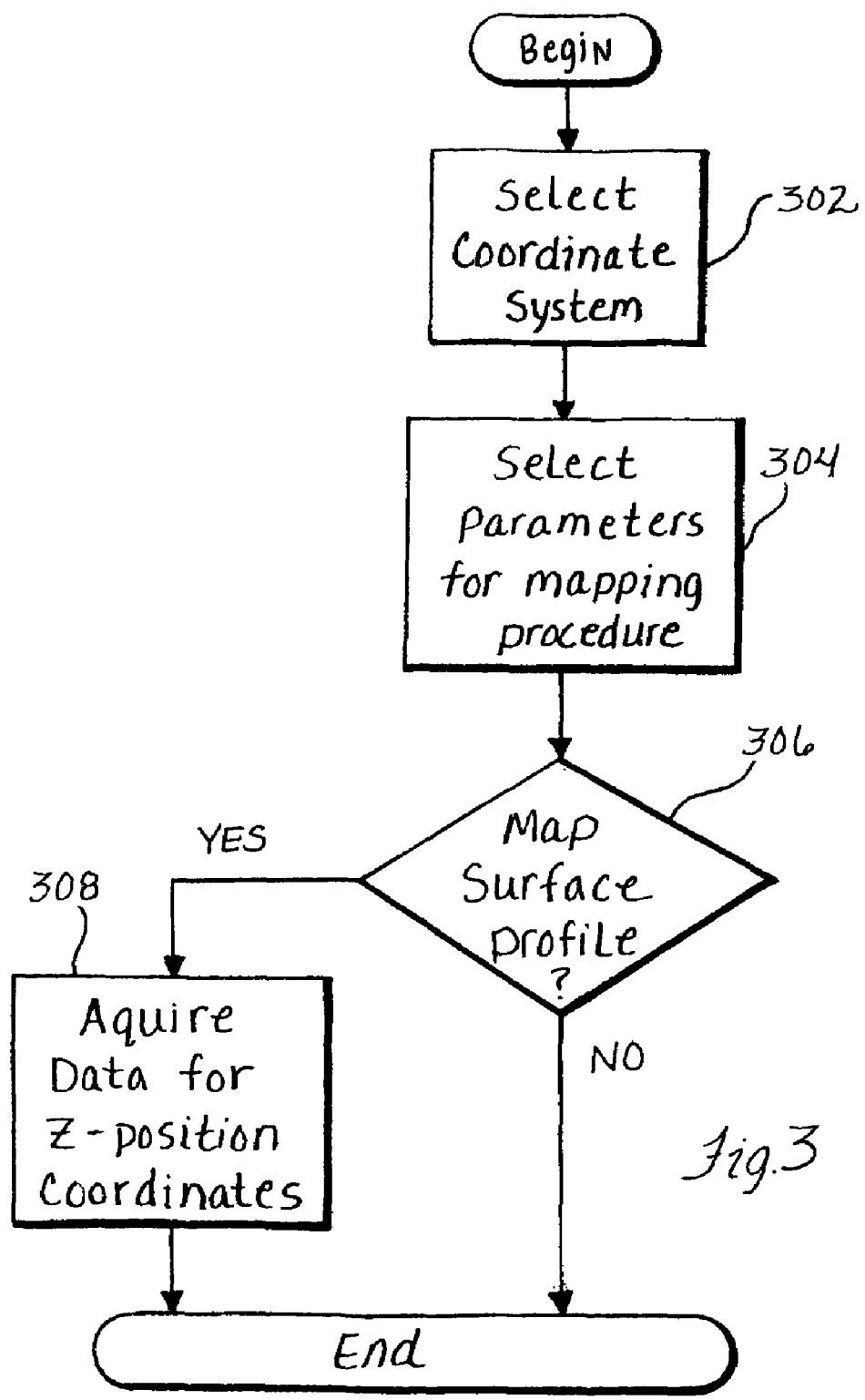
FIG. 3 is a flowchart of a method for selecting graphical display parameters in accordance with the method of FIG. 2.

Referring now to FIG. 3, one example of a corresponding method to accomplish the above-mentioned steps is described. At step 302, a coordinate system is selected by an operator. The operator may choose any number of coordinate systems to display the information. For example, the operator may choose a circular coordinate system to display graphs, where the coordinates are mapped according to radius and angle. The operator may also choose the polar map coordinate system, the three-dimensional coordinate system (where the coordinates are given in terms of the x, y, and z positions), or the annular coordinate system (where data is graphed into rings). The operator may also choose to map the physical contours of the portion of the part under test. The operation of this mode is described in copending application Ser. No. 09/539,346, "X-Ray Diffraction Apparatus and Method," which has already been incorporated herein by reference in its entirety.

At step 304, the operator can set parameters related to the display of the graph. For example, if the coordinate system being used is the three-dimensional coordinate system, then the operator may input x and y dimensions for the graph, and x and y resolutions for the graph. The operator may also choose to have data displayed on this graph in real-time. In other words, the operator may have the data displayed to the user as the data is collected by a measurement system. In another example, the operator may determine an analysis method that is to be used in analyzing the data, for instance, the Single Exposure Technique, the Linear technique, the Elliptical analysis method, or the Triaxial analysis method.

At step 306, it may be determined if the z-axis profile of the part under test should be mapped. If the answer is affirmative, at step 308 the system acquires data for the z-position coordinates. The values of the z coordinates are mapped so that, for example, an energy emitter can properly focus the energy on the part under test. If the answer is negative, then execution ends.

Figure 4:
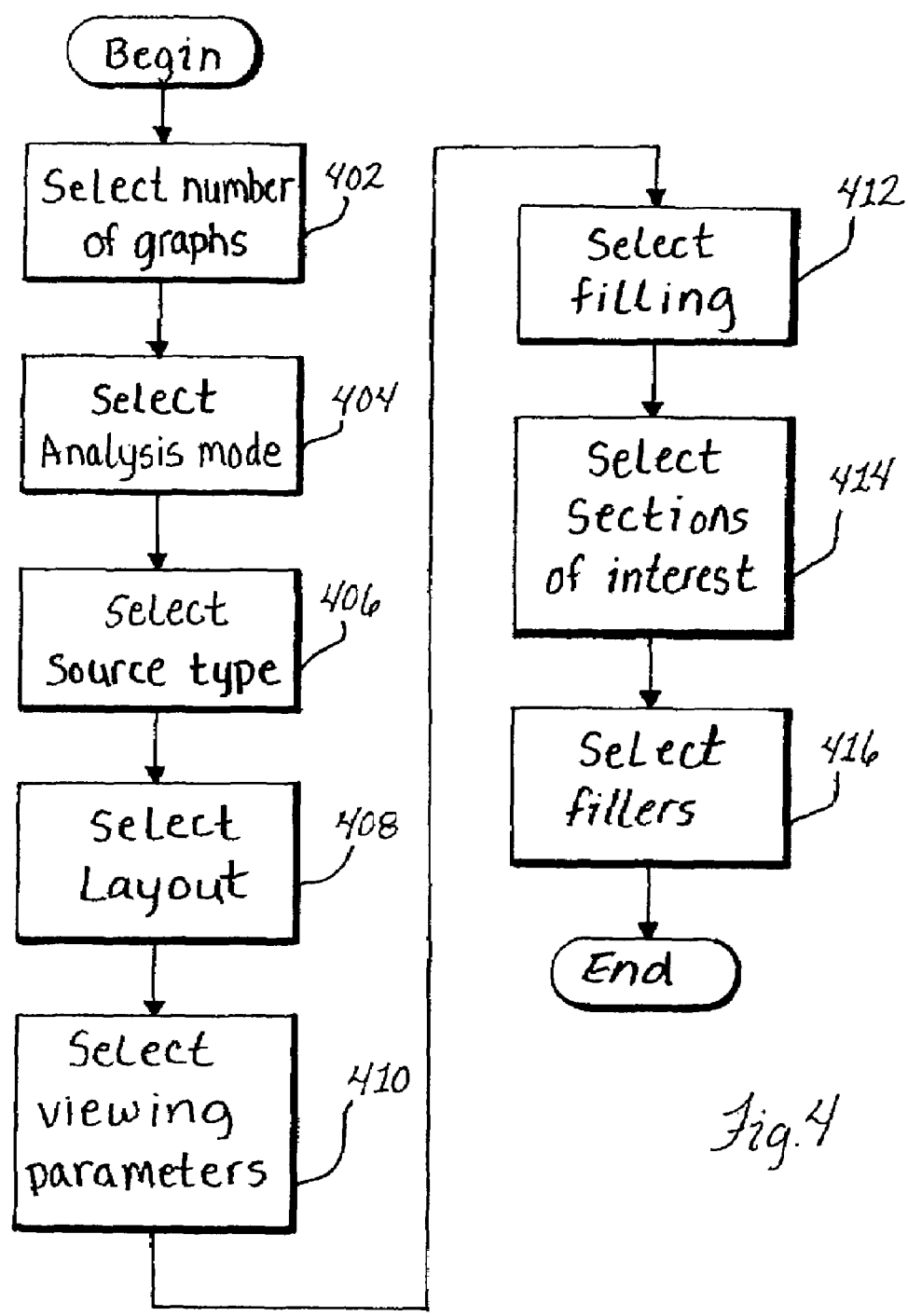
FIG. 4 is a flowchart for selecting additional display parameters in accordance with the method of FIG. 2.

Referring now to FIG. 4, one example of a corresponding method to accomplish the above-mentioned actions is described. At step 402, the operator may select how many graphs are to be simultaneously displayed on a single screen. Any number of graphs can be displayed such that the graphs are visually discernable and recognizable by an operator. In one example, the operator may chose to display four graphs. When displayed, the graphs may be oriented along a common axis, for example along a vertical axis so that the graphs are "stacked" upon each other.

As previously discussed, it is advantageous to stack the graphs on top of each other on a single screen to enhance the ability of the operator to readily make visual comparisons. For example, they can examine the graphs and compare the values for a particular region of the part under test. As stated earlier, by using this approach, there is no need to switch back and forth between different computer screens and no need to maintain two terminals in order to make visual comparisons.

Alternatively, the graphs may be overlapped. In other words, instead of stacking the graphs one on top of each other, the graphs may be displayed together on the same x-axis and y-axis. In this case, two or more graphs can be displayed using different colors. In still another example, the graphs may be displayed so that they are horizontally aligned along their respective x-axes.

At step 404, the operator may select an analysis mode. In one example, the operator may choose to analyze the actual data collected. In another example, the operator may choose to analyze previously collected data using map algebra. For example, values contained in a second map may be subtracted from the values contained in a first map creating a third, "difference" map. Other options for the analysis mode are possible.

In another approach, a user can retrieve a graph from memory relating to a particular material characteristic. A second graph showing the same material characteristic, either related to a current set of measurements or generated during a second time period, can also be displayed. The first and second graphs may relate to the same or different parts under test. The user can drag the first graph and drop it on the second graph, and then click their computer mouse to generate a third graph, which illustrates the differences between the first and second graphs. By using this approach, the viewer can readily determine how a particular material characteristic has changed over time between parts or on the same part.

At step 406, the operator may select the material characteristics to be displayed in a graphical format. The characteristics to be displayed to the operator may be selected as a group (i.e., as a set) or individually. In one example, the operator may select source data types based upon a measurement method (e.g., linear, elliptical, or triaxial). In another example, the operator may select characteristics individually. Examples of characteristics include but are not limited to stress, stress error, intensity ratio, average peak breadth, average full width at half maximum (FWHM), shear stress, stress tensor, error tensor, x- direction stress, y-direction stress, maximum shear, equivalent stress, hardness, grain size, dislocation density, plastic strain, percent plastic strain, percent cold work, phases, percent retained austenite, strain, strain error, shear strain, strain tensor, x-direction strain, y-direction strain, and maximum strain to name a few. The characteristics may be determined at the surface of the part under test or at particular depths underneath the surface of the part under test. In addition, the characteristics may be derived from the detected diffracted or attenuated energy. As is apparent from the forgoing, a broad range of characteristics and selection methods are possible with the present system and method.

At step 408, the operator may select the layout of the display. The operator may determine the positions on the screen where graphs and other information is to be displayed. For instance, the operator may indicate the exact screen coordinates where each graph is to be displayed on the screen. This may be accomplished by clicking and dragging the graphs with a computer mouse or some other selection method. Custom setting is advantageous because it allows the operator to alter the display from predetermined setting based upon actual measurements. In addition, it allows the operator to determine the display and location of graphs that are truly useful in evaluating the part under test.

The operator may also choose to display the graphs according to predetermined positioning patterns. For instance, the operator may decide to display three-dimensional graphs along the left side of the screen along a common vertical axis and two-dimensional graphs along the right side of the screen. This is advantageous whenever the operator needs to quickly display the graphs without having to take the time to custom program each graph location.

The operator may additionally select a convenient layout method to facilitate the comparison of information included in the graphs. For instance, the operator may "stack" graphs by aligning multiple graphs along a common vertical axis. In another example, graphs may be aligned horizontally along a common horizontal axis. The operator may do this using a programming tool to determine a common axis and move the graphs to this common axis. For instance, the operator may use a computer mouse to drag and drop the graphs along the axis or alternatively specify an x, y coordinate to align the graphs. Other alignments and positioning patterns are possible. As has been discussed previously, the alignment pattern aids the viewer in evaluating the graphs of the material characteristics.

The operator may also display an analysis report for a single point on a graph. For instance, the operator may move a cursor to a point or area on a graph and click on the point causing a report to be generated and displayed concerning that point. In one example, the report includes stress-related information obtained from diffracted energy at two sensors. Other examples of reports are possible.

Once the graphs have been displayed, the operator may also move graphs on the display. For example, the operator may use a cursor control to move any graph to a new position to facilitate additional comparisons between graphs. Other examples and methods for determining and adjusting the layout of the screen are possible.

Conveniently, if the resolutions and scales of each of the graphs are the same or similar and the graphs are aligned, then easy comparisons may be made between different material characteristics of portion of the part under test. This aids viewing since an area of the same size will be presented to the user for each of the graphs. In other words, the user does not have to struggle to see small areas and compare the areas to other larger areas for other material characteristics if the same scale is chosen for the x and y axes.

In addition, the scale and resolution of the z-axis may also be adjusted for each of the graphs. The graphs for each of the material characteristics may have different ranges for the measured values of the characteristic and the ranges can be preferably adjusted by the operator so that the operator can easily discern variations in the measurement values for the characteristic. For example, and now also referring to FIG. 7, it can be seen that scale for the graph showing stress varies from approximately 27 to −90 ksi; the graph showing shear stress varies from approximately 17 to −10 ksi; the graph showing intensity ratio varies from 1.8 to 1.0 ksi; and the average peak FWHM varies from 3.8 to 2.1 ksi. By varying the resolutions, the operator can easily variations in the measurements and make meaningful comparisons between the graphs.

At step 410, the operator may select viewing parameters such as rotation, translation, zoom, resolutions for the x, y and z axes; tensile compression; and spectrum (color gradient). At step 412, the operator may select the map surface fill for three-dimensional maps. For example, as is known in the art, the operator may select points fill, wire frame, or surface fill as the surface fill type. Manifestly, other examples of viewing parameters and surface fill types are possible.

At step 414, the operator can inspect characteristic values as a function of dimensional coordinate. For example, the operator may display the characteristic as a new graph and as a function of position along the x, y, or z axis. In another example, the operator may also create an isobar projection of the graph to display.

At step 416, the operator may select filters, which adjust the content and/or layout of the graphs on the display. For example, the operator may remove a region from a graph being displayed because the data from the region is suspect or unreliable. As is described in greater detail elsewhere in this application, the operator may also set measurement thresholds whereby predefined actions occur when these thresholds are reached. In addition, as will also be described in greater in this application, the operator may have the system monitor the graphs for certain evaluation guides and may have the system perform certain actions when these guides have been detected. The evaluation guides 1402 themselves may be the subject of graphs (see FIG. 14), such as when there is a correlation between values of the different measured material characteristics and the threshold for action as determined by such a guide.

Figure 5:
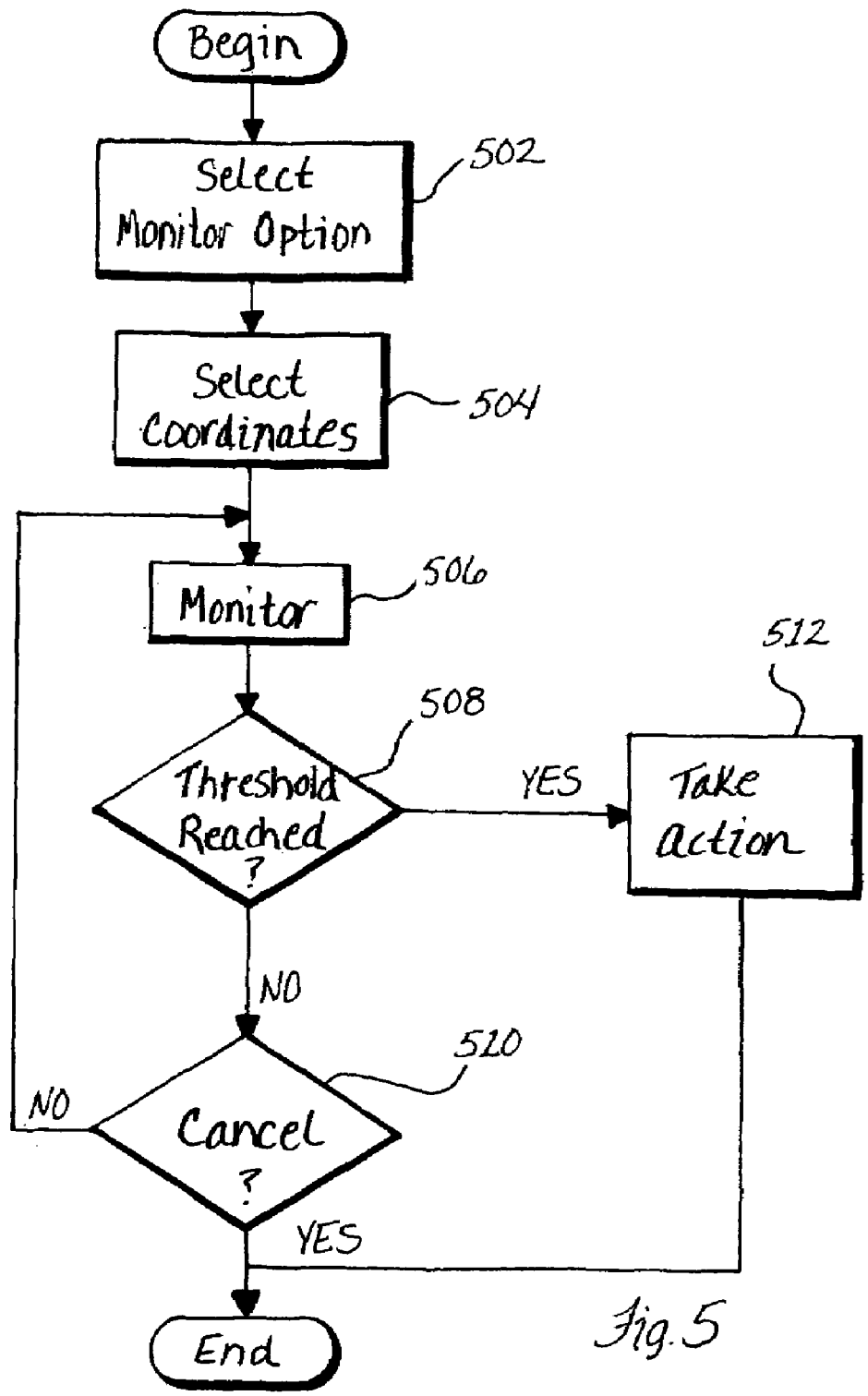
FIG. 5 is a flowchart for monitoring threshold values of a coordinate and taking an action in accordance with the method of FIGS. 2–4.

Referring now to FIG. 5, one example of a method corresponding to the above-mention actions is described. At step 502, the monitor option for monitor mode may be selected for a graph by an operator. This selection allows data to be displayed in the graph in real-time, as the data is measured and collected. Periodic updates may also occur.

At step 504, the operator may determine the coordinates within the graph that are to be monitored. In one example, an area (multiple points) of the graph is monitored. In another example, a single coordinate within the graph is selected. The operator may then set predetermined threshold values that are to be monitored for the selected points for certain material characteristics. The threshold values may be related, for instance, by a mathematical relationship.

At step 506, the system may monitor the area or point of the graph. As is known in the art, any combination of electronic hardware or computer software may be used to accomplish this result.

At step 508, the system can determine whether a threshold has been reached. If the answer is affirmative, then execution continues at step 512. If the answer is negative, then execution continues at step 510. The system may determine whether some or all of the thresholds have been reached at the selected points.

At step 510, the system may determine if the operator wishes to cancel the monitoring. If the answer is affirmative, execution ends. If the answer is negative, control returns to step 506.

At step 512, an action can be taken. For example, the system may alert the operator by raising a flag or alarm on a video screen. In another example, the system may send a communication, for instance, an e-mail or a wireless message, to the operator or others. The content of any communication may be used to alert the operator that a part having suspicious characteristics has been detected. This may necessitate further action by the operator. For instance, it may mean removing the part or testing the part again, for different material characteristics. Other actions are possible.

Figure 6:
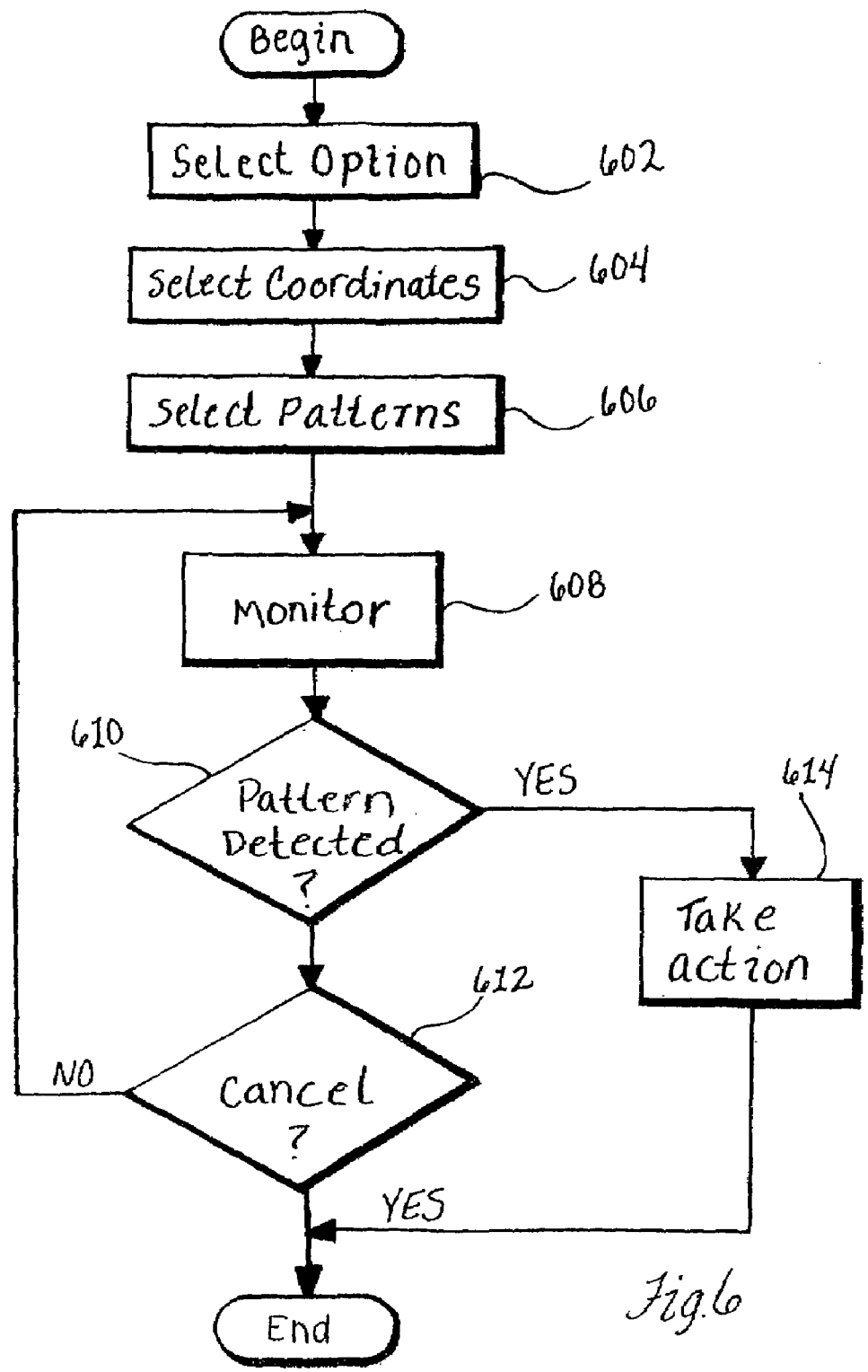
FIG. 6 is a flow chart for monitoring patterns of values defined by an evaluation guide in accordance with another preferred method of the present invention.

Referring now to FIG. 6, one example of a corresponding method for monitoring the graphs for evaluation guides is described. At step 602, the monitor option for monitor mode may be selected for the graph by the operator. This selection allows the graph to be displayed to the operator in real-time, as the data is measured and collected.

At step 604, the operator can determine a coordinate to be monitored within a graph. In another example, an area of the graph is selected to be monitored.

At step 606, the operator may determine an evaluation guide. The evaluation guide may include any set of guide values relating to at least one material characteristic. As between evaluation guides, the guide values may be related by a known relationship, unrelated, or determined by testing. In addition, the guide values contained within an evaluation guide may be predetermined or determined by the operator as needed. Further, the guide values associated with an evaluation guide may be fixed, or an operator may change the values in the guides over time such as based on the empirical data gathered on parts via a testing system as described herein.

In one example, an evaluation guide may be selected having a stress value of S1 and a retained austenite value of A1. The operator may also indicate that a first action is to taken, if these guide values are detected. In another example, the operator may determine guide values of stress of S2 and a retained austenite of A1. The operator may also indicate that a second action be taken when the values in this evaluation guide are detected.

At step 608, the system can monitor the area of the graph in an attempt to obtain a match with the guide values. As is known in the art, a combination of electronic hardware or computer software may be used to accomplish this result.

At step 610, the system may determine whether the guide values have been detected. If the answer is affirmative, then execution continues at step 614. If the answer is negative, then execution continues at step 612.

At step 612, the system can determine if the operator wishes to cancel the monitoring. If the answer is affirmative, execution ends. If the answer is negative, control returns to step 608.

At step 614, an action may be taken. The action can be defined by the operator as discussed above with respect to step 606. For example, the system may alert the operator by raising a flag or alarm on the screen. In another example, the system may send a communication, for instance, an e-mail to the operator or others. The content of such a communication may be used to alert the operator that a part having suspicious characteristics has been detected. This may necessitate further action by the operator, for instance, removing the part or testing the part again, for new characteristics. Other actions are possible.

Referring to FIGS. 7–12, there are illustrated examples of displays created by the above-mentioned steps. Preferably, these displays may be made on a single screen 108*a* of a video monitor to facilitate ease in the comparison between the different graphs as has been previously described. It will be understood that the graphs described herein are only examples. In other words, the content, type of graphs, features, relationships between graphs, information displayed, type of reports, contents of the reports, analyses, charts, or tables may vary. In addition, the locations, color, graphical fill, shading, or any other font or stylistic feature may be changed or altered. Finally, the graphs are shown as being in the three-dimensional (x, y, z) coordinate system. However, it will be understood that the graphs can be mapped into any other coordinate system and that graphs of different coordinate systems can be displayed together.

Referring now to FIG. 7, one example of a display on a single screen 108*a* will be described. The display includes four graphs stacked 702, 704, 706, and 708 on top of each other on a single screen. To facilitate comparisons, the four graphs are mapped on the same coordinate system, with the same resolution, and are aligned along a common vertical axis. This allows a viewer to see the magnitude of each of the measured material characteristics that are graphed at the same location on the tested part by simply scanning substantially vertically up and down along the screen 108*a*. In this example, the operator has chosen to display four material characteristics (using the four graphs 702, 704, 706, and 708) including stress, shear stress, intensity ratio, and average peak FWHM. The graphs 702, 704, 706, and 708 may be color-coded where different colors indicate different measurement value ranges. In one example, a particular shade of red may indicate shear stresses between 16.8 and 14.4 ksi, and another shade of red may indicate stresses between 14.4 and 11.5 ksi. A color gradient chart next to each of the graphs indicates the relationship between color and measurement value.

By aligning the graphs 702, 704, 706, and 708 along a common axis, it can be seen that easy visual comparisons may be made as to the material characteristics displayed. In this case it can be seen that stress is relatively constant for one portion of the part rising to a uniform higher value on the other portion of the part under test. It can also be seen that the shear stress is relatively constant over the part except for a peak in one area of the part. Intensity ratio can be seen to vary widely reaching different peaks in different areas of the part under test. Average peak width FWHM can be seen as relatively constant but dipping in one area of the part under test. If it were a requirement that both stress and shear stress be high for a particular region before an action is needed, a viewer could easily determine that this requirement is not met and no further action need be taken.

Referring now to FIG. 8, another example of a display will be described. This display includes four graphs 802, 804, 806, and 808, and report 810. As with the display of FIG. 7, the display includes four graphs stacked on top of each other. To facilitate comparisons, the four graphs 802, 804, 806, and 808 are mapped on the same coordinate system, using the same resolution, and are aligned along a common vertical axis. The operator has chosen to display four material characteristics including stress, shear stress, intensity ratio, and average peak FWHM. A color gradient chart next to the graphs indicates the color and measurement relationships. The graphs are the same as shown in FIG. 7.

The report 810 may be created when the operator clicks on a particular point in a graph. The report 810 can be any series of values relating to a point or set of points selected by the operator. In this example, the report 810 indicates different values related to diffraction information received at two sensors from the part under test. Some of these values can be mapped in two-dimensions in the graph in the center of FIG. 8.

D-spacing is a lattice parameter and relates to the spacing between the crystal planes of the material while $\sin^2 psi$ relates to the diffraction angle of the sensed diffracted energy. The slope of the plotting of d-spacing verus $\sin^2 psi$ is the strain of the part. Additionally, when $\sin^2 psi$ and d-spacing from two separate detectors are plotted on a single graph, any separation between the two plottings indicates that shear stress is present in the part.

Conveniently, this type of information can be displayed to a viewer. Specifically, a two-dimensional graph 812 includes a mapping of $\sin^2 psi$ versus Dspacing from the report 810. The graph 812 shows a first plotting 811 for values at a first detector and a second plotting 813 for values at a second detector. Thus, in this example, a user can examine the lines 811 and 813, determine that the lines do not coincide, and determine that shear stress is present.

The report 810 may be used by the viewer to determine the exact value of stress at the particular point associated with the report. This is advantageous in situations where the viewer needs to know the exact value to determine if the value exceeds a threshold. In the case of FIG. 8, the operator may have to determine if the stress at a point exceeds 12 ksi, examined the stress graph 802, and was unable to ascertain the exact value of stress at that point on the part. However, the operator can generate the report 810 and see that the stress value 12.469 ksi. Hence, the operator can take appropriate action based upon viewing the report.

Figure 9:
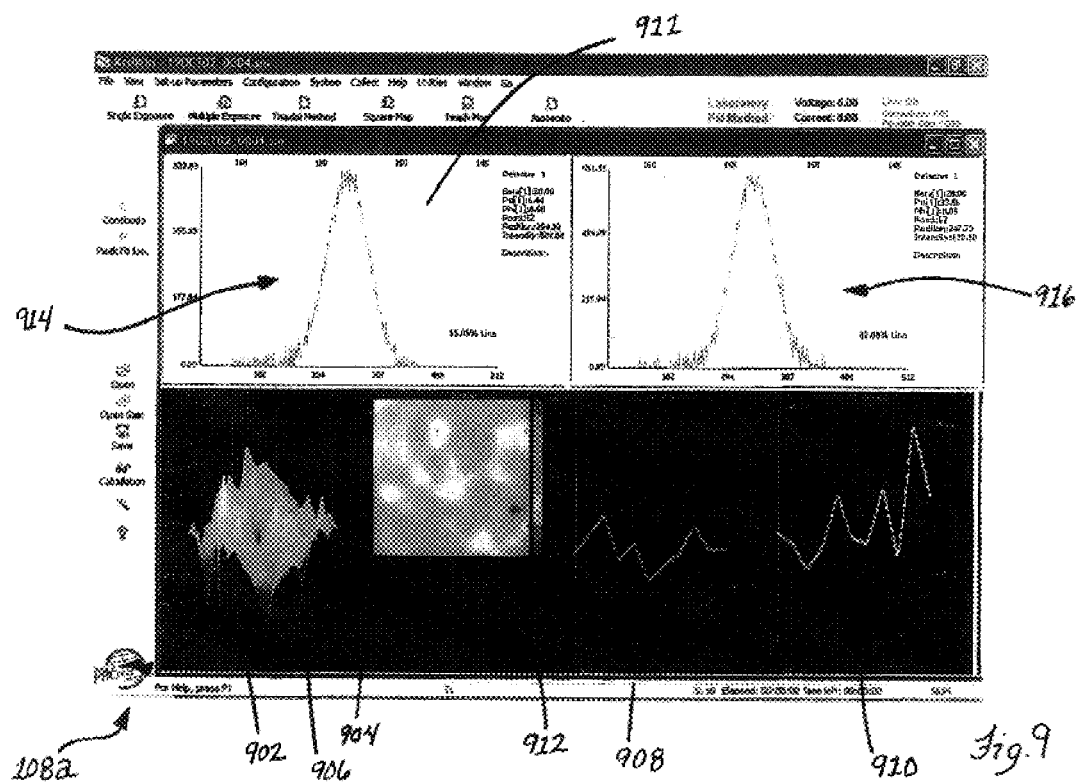
FIG. 9 is a single screen display showing two and three dimensional graphs of tested material characteristics.

Referring now to FIG. 9, yet another example of a display is depicted. The display illustrated in FIG. 9 includes a three-dimensional graph 902. Two planes 904 and 906 pass through the three-dimensional graph 902. Plane 904 lies in the x and z-directions and plane 906 lies in the y and z-directions. The information contained within the two planes 904 and 906 is transposed onto two charts 908 and 910 shown at the bottom right portion of the display. The first chart 908 illustrates values from the three-dimensional graph as a function of x-position and the second chart 910 illustrates values from the three-dimensional graph as a function of y-position.

In addition, the display includes an isobar map 912 derived from the three-dimensional graph 902. This isobar map 912, to the right of the three-dimensional map 902, shows a two-dimensional projection of the three-dimensional graph 902 where measurement values falling within certain ranges are given the same color. The isobar map is color coded so that the operator can easily determine variations in the material characteristic. For example, it can be seen that several regions have excessive high and low values. On the top, the display also includes two graphs 914 and 916 giving the x-ray diffraction information as measured at a first detector and as measured at a second detector. As can be seen, the intensity of the diffraction peaks at about the same angle for each of the detectors.

Referring now to FIG. 10, still another example of a display is illustrated. The display includes a three-dimensional graph 1004 of stress, diffraction peak measurements graphs 1006 and 1007, a stress report 1002, and a graph 1003 of D-spacing versus sine squared psi.

The two diffraction peak graphs show that the diffraction peak intensity is maximized at a particular angle at both detectors. The graph 1004 shows that stress is maximized at a particular point. The remaining areas of the graph show that stress is low for the area shown of the part under test. The graph 1004 may reflect that the part under test has a particular problem at the point of high stress. If this is the situation, then the operator may perform some action, for instance, pull the part or perform further tests. The report 1002 shows various values as measured at two detectors. Some of these are graphed (D-spacing versus $\sin^2 psi$) in graph 1003 so that the operator may make a determination as to whether strain and shear stress are present.

Referring now to FIG. 11, another example of a display is illustrated. This display shows three-dimensional graphs, aligned along a common z-axis to facilitate making easy comparisons. A stress graph 1102 indicates that stress is maximized in an area 1102. This may indicate to the operator that the part under test is exhibiting problems in that area and that further action is required. A graph 1103 shows the stress error over the area of the part under test. It can be seen that the error varies considerably from point to point, although it is maximized at particular points. A graph 1104 shows the intensity ratio for the area of the part under test. Again, as can be easily seen, the intensity ratio varies considerably over the area of the part under test reaching maximums at several points. Finally, a graph 1105 shows the average peak breath for the area of the part under test. Again, this varies widely over the part under test with no sole maximum or minimum areas.

The scales for each of the graphs 1101, 1103, 1104, and 1105 have been custom set by the user. Thus, the scale for the graph 1101 is 874.6 to −271.1 psi; the scale for the graph 1103 is 10.5 to 0.0; the scale for the graph 1104 is 1.1 to 1.0 and the scale for the graph 11-5 is 3.3 to 3.0. Setting the scale to a uniform range would not be acceptable or convenient for viewing since a scale that shows distinct variations in stress would not show variations in intensity ratio very well.

The display of the graphs on top of each other facilitating the visual comparisons of the characteristics. For example, if the operator were looking for particular areas of the graph where stress were high, they would easily identify the area 1102 of the graph 1101 as an area of high stress. If they were also looking for where the error, intensity ratio, and average peak breath were not uniform but varied considerably, they could also easily identify that the other graphs 1103, 1104, and 1105 fit that criteria. Thus, the operator could easily take further action upon making a visual evaluation of the graphs 1101, 1103, 1104, and 1105.

Figure 12:
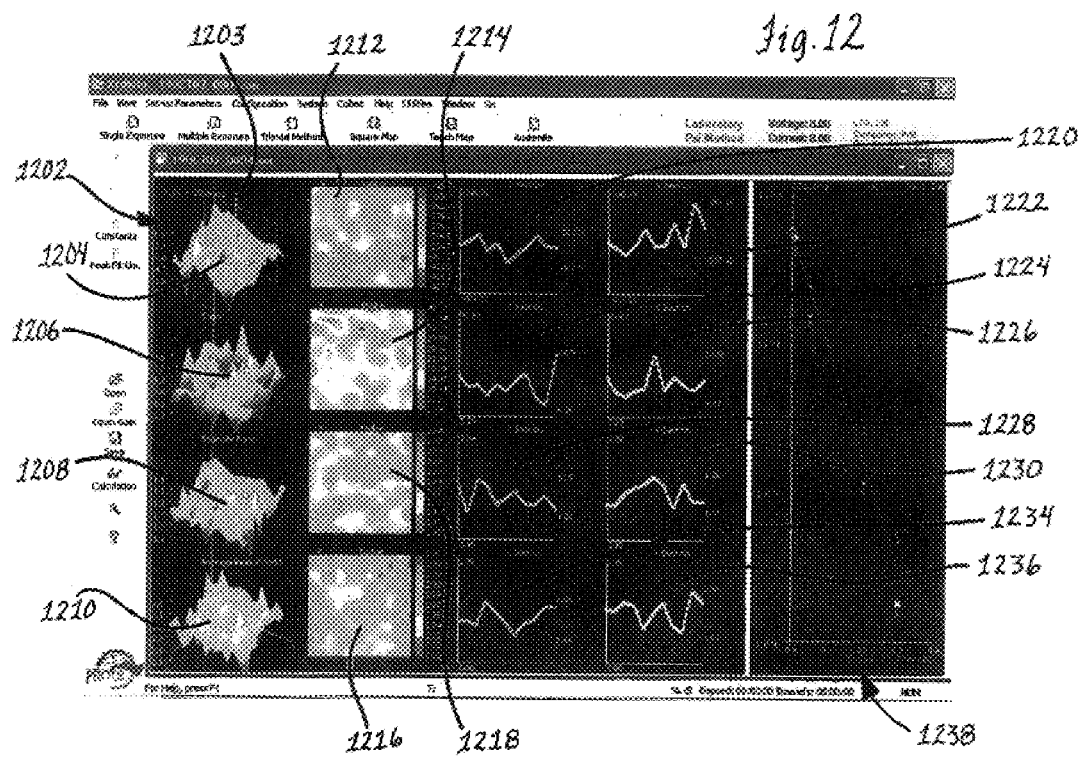
FIG. 12 is a single screen display of graphs showing different material characteristics along a common axis, isobar graphs and two dimensional graphs.

Referring now to FIG. 12, yet another example of a display is described. This display shows four graphs 1202, 1206, 1208, and 1210 aligned along the vertical z-axis. Specifically, the graph 1202 shows stress. As can be seen, stress varies considerably over the area of the part under test being tested. Planes 1203 and 1204 are used to show how stress varies in two dimensions. The graph 1220 shows the section 1204 where stress is graphed as a function of x-position. Similarly, the graph 1222 shows the section 1203 where stress is graphed in the y-direction. It can be seen that in the graphs 1220 and 1222, stress varies but reaches its highest value in the y-direction.

The graph 1212 is an isobar graph of stress. It can be seen that stress reaches a peak value in the bottom right portion of the graph 1212. It is apparent that a viewer can examine the isobar graph 1212 and easily determine the locations of the maximum and minimum values of stress.

The graph 1206 shows stress error. As can be seen, stress error varies considerably over the area of the part under test being tested. The same planes 1203 and 1204 are used to show how stress error varies in two dimensions. The graph 1224 shows the section 1204 where stress error is graphed as a function of x-position. Similarly, the graph 1226 shows the section 1203 where stress error is graphed in the y-direction. It can be seen that in the graphs 1224 and 1226, stress error varies but reaches its highest value in the x-direction.

The graph 1214 is an isobar graph of stress error. It can be seen that the peaks of stress error are easily discernable as dark colors in the upper part of the graph 1214. As with stress, it is apparent that a viewer can examine the isobar graph 1212 and easily determine the locations of the maximum and minimum values of stress error.

The graph 1208 shows intensity ratio. As can be seen, intensity ratio varies considerably over the area of the part under test being tested. The same planes 1203 and 1204 are used to show how intensity ratio varies in two dimensions. The graph 1228 shows the section 1204 where intensity ratio is graphed as a function of x-position. Similarly, the graph 1230 shows the section 1203 where intensity ratio is graphed in the y-direction. It can be seen that for the graphs 1228 and 1230 intensity ratio varies but does not reach overall peaks as in the graphs related to stress and stress error.

The graph 1218 is an isobar graph of intensity ratio. It can be seen that the intensity ratio is more uniform over the coverage area and lacks the strong highs and lows present in the other isobar graphs.

The graph 1210 shows average peak FWHM. As can be seen, average peak FWHM varies considerably over the area of the part under test being tested. The same planes 1203 and 1204 are used to show how average peak FWHM varies in two dimensions. The graph 1234 shows the section 1204 where intensity ratio is graphed as a function of x-position. Similarly, the graph 1236 shows the section 1203 where intensity ratio is graphed in the y-direction. It can be seen that for the graphs 1234 and 1236 intensity ratio varies widely in both directions.

The graph 1216 is an isobar graph of intensity ratio. It can be seen that there are several peaks in the upper portion of the graph that are easily detectable by the viewer. As with stress and stress error, it is apparent that a viewer can examine the isobar graph 1212 and easily determine the locations of the maximum and minimum values of average peak FWHM.

It can be seen that the display in FIG. 12 can be used in a multitude of ways to aid an operator in determining the reliability of the part under test. In one example, the viewer can examine the graphs 1202, 1206, 1208, and 1210 to easily compare the measured values of the material characteristics. Then, the viewer may determine that they are interested in viewing the characteristics only in the planes 1203 and 1204. The planes 1203 and 1204 can be defined by the user, applied to each of the graphs, and the plurality of x and y cross sectional graphs generated. Then, the user may compare the cross sectional graphs to each other to further the comparison, for example comparing the x-cross section of stress 1220 to the x-cross section of stress error 1224. Finally, the user can easily examine the isobar graphs to determine where the relative peaks were to determine if there were areas of interest requiring further investigation.

Figure 13:
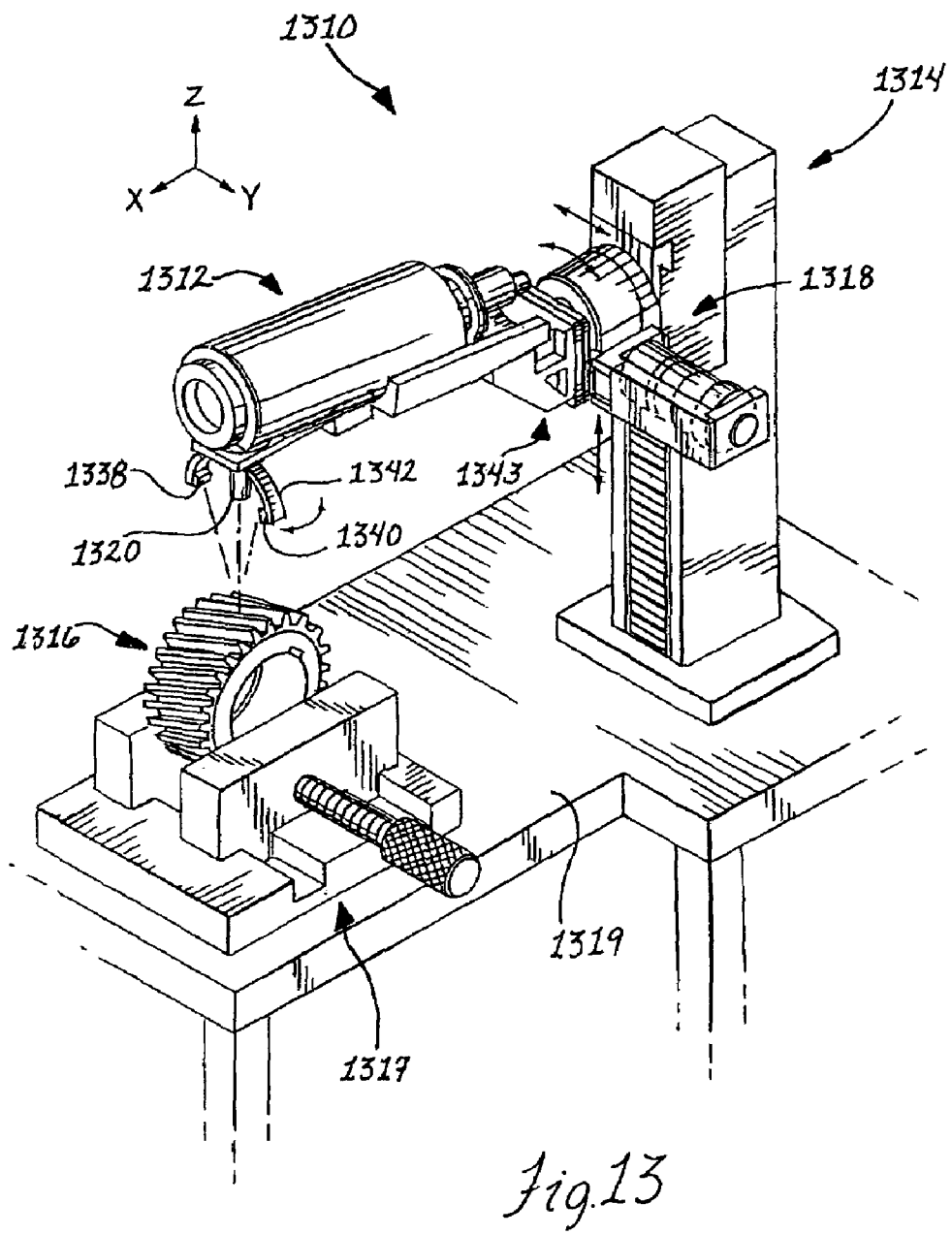
FIG. 13 is a perspective view of an energy diffraction apparatus for x-ray diffraction testing of parts.

Referring now to FIG. 13, one example of an energy measurement system as disclosed in pending U.S. application Ser. No. 10/390,479, filed Mar. 1, 2003, used to obtain measurements is next described. In this example, the energy measurement system is an x-ray diffraction apparatus 1310 and includes a modular x-ray goniometer head 1312 that is detachably connected to a base unit 1314 for taking x-ray diffraction measurements from various parts such as the illustrated gear 1316 rigidly held by fixturing 1317 below. The x-ray head can be shifted in a plurality of different linear directions such as in the vertical z-axis direction as well as in the lateral y-axis direction, as shown. X-axis fore and aft direction shifting can also be provided as well as rotary or pivot shifting of the head 1312 about different pivot axes. A common drive assembly 1318 shifts the x-ray tube head assembly 1312, and particularly the emitter or collimator 1320 depending from the tube housing 1312a at the forward end portion thereof in arcuate path 1322 so that as the tube oscillates back and forth in its arcuate path 1322, x rays are directed at the region on the part 1316 from a variety of different angles to provide several different dat points from which measurement information can be gleaned. Frame 1319 of the base unit 1314 can support both the part 1316 along with its fixturing 1317 and the drive assembly 1318.

Also, specially dedicated x-ray heads can be used of various sizes. In one example, the x-ray head 1312 can be employed where higher power requirements are required for generating x-rays to take measurements from a particular part material, whereas smaller heads can be used where the power is not as critical and access to difficult part geometries is needed. In particular, smaller heads can be maneuvered into confined spaces such as found inside on the interior of tubular parts for taking x-ray measurements from the interior surfaces thereof. Head assembly is specially adapted for taking measurements from small through bores that are of a relatively shallow depth such as the illustrated bolt holes found in aircraft rotor discs.

Beyond size, the modular heads can be tailored in several other respects as well. For example, the wavelength generated for the x-rays can be tailored to the material to be measured so as to better match the lattice structure thereof. The beam shape can be tailored to the piece to be measured as by providing different collimators 1320 on the various x-ray heads. For example, for those pieces that have surfaces in long narrow crevices or holes that are desired to be measured, the collimator 1320 can be configured to generate a narrower x-ray beam to avoid measurement errors.

In addition to the collimator, an x-ray detector assembly is provided as carried by each of the x-ray heads including x-ray detectors or sensors 1338 and 1340 that are typically mounted on either side of the collimator 1320 via an arcuate x-ray mount 1342. The detectors may be any type of sensors used to detect x-rays, for instance, fiber optic sensors. The x-ray heads can have the position of these detectors 1338 relative to the collimator 1320 varied along the mount 1342 or on differently sized mounts 1342 from one head to the other so that they are matched with the x-ray wavelength generated by the head and the response of the material for which the x-ray head is to be used for taking x-ray diffraction measurements from. The mount 1342 itself can be shifted to provide for different measurement techniques or to accommodate different diffraction angles such as in assembly head. As is apparent, the provision of modular x-ray heads enables much greater flexibility in tailoring the apparatus to the particular needs of the x-ray diffraction operation that is to take place without necessitating several different x-ray diffraction units for this purpose.

An electronic control system 1343 can be used that can interconnect the sensors 1338 and 1340 on the mount 1342 to the control system 1343. The link between the electronic control system 1343 and the sensors on the mount 1342 may be any electrical link, for instance, an electrical or fiber optic cable. The electronic control system 1343 may control the movement and operation of the sensors 1338 and 1340 as well as the emitter 1320. The electronic control system 1343 is further coupled to the display processing system, for instance, the controller 102 in FIG. 1, and this connection may also be by electrical or fiber optic cable.

Referring now to FIG. 14, one example of a graph showing the characteristics of an evaluation guide is illustrated. As shown in FIG. 14, a line 1402 is used to graphically display the relationship between stress and shear stress. As can be seen, the line 1402 defines a linear relationship where, as stress increases, shear stress also increases. The line 1402 may represent an expected relationship or a threshold. In other words, the line 1402 may indicate a target on or around which measurement values should fall or, alternatively, a threshold where if values fall above or below the line 1402, appropriate action may be required.

The evaluation guide represented by the line 1402 is graphed in an x,y plane and, consequently, test measurement resultants, representing the measurement values of material characteristics can be plotted against the guide values. For instance, for a point on the part under test having a stress measurement value of S1 and a strain measurement value of SS1, a test measurement resultant of (S1, SS1) can be formed. Conveniently, this test measurement resultant can be plotted as a point (i.e., (S1, SS1)) on the graph with S1 representing a value on the x-axis and SS1 representing a value on the y-axis. The location of the point (S1, SS1) can be compared to the line 1402 and an action taken as described herein.

While there have been illustrated and described particular embodiments of the present invention, it will be appreciated that numerous changes and modifications will occur to those skilled in the art, and it is intended in the appended claims to cover all those changes and modifications which fall within the true spirit and scope of the present invention.

What is claimed is:

1. A computer-implemented method for displaying graphical information indicative of a plurality of material characteristics for a portion of a part under test, the method comprising:

directing x-ray energy at the portion of the part under test;

detecting a single stream of diffracted energy from the portion of the part under test, the single stream of diffracted energy formed by interaction of the x-ray energy with the part under test, the single stream of diffracted energy being directly simultaneously indicative of a plurality of first order material characteristics of the part under test;

analyzing the single stream of diffracted x-ray energy and determining a first material characteristic and a second material characteristic for the same portion of the part under test and from the same single stream of diffracted x-ray energy;

forming a first graph and a second graph based upon the single stream of diffracted x-ray energy, the first graph relating to the first material characteristic and the second graph relating to the second material characteristic;

displaying the first and second graphs in a manner that facilitates simultaneous visual comparisons between the information contained in each of the graphs; and determining by a human operator whether a relationship between the first and second material characteristics exists in the portion of the part under test that bears on a condition of the part under test based upon the simultaneous visual comparison afforded by the display of the first and second graphs.

2. The method of claim 1 wherein the step of displaying the first and second graphs includes displaying the first and second graphs on a single screen.

3. The method of claim 1 wherein displaying the first and second graphs includes displaying each of the first and second graphs using a common resolution and includes aligning the first and second graphs along a common axis to facilitate easy and accurate evaluation and comparison of the first and second material characteristics.

4. The method of claim 1 wherein displaying the first and second graphs includes relating selected information in the first and second graphs to color intensity so that variations in the color intensity are based upon variations in the selected information and displaying the selected information using the color intensities for highlighting variations and differences in the first and second material characteristics.

5. The method of claim 1 wherein displaying the first and second graphs includes displaying a three-dimensional graph and including selecting a two-dimensional portion of the three-dimensional graph for facilitating the evaluation of the material characteristic as a function of a position along an x-axis or y-axis of the graph.

6. The method of claim 1 wherein displaying the first and second graphs includes displaying an isobar graph illustrating and highlighting differences and variations in the information included in the graph.

7. The method of claim 1 wherein the displaying of the first and second graphs includes displaying a selected ones of the first and second graphs in real-time as the data is obtained to allow for the efficient and timely evaluation of data by an operator as part testing occurs.

8. The method of claim 1 wherein detecting a single stream of diffracted energy includes obtaining diffracted energy for each of the first and second graphs at different points in time and wherein determining the first and second material characteristics comprises applying calculus operations and evaluation procedures on the data obtained at different points in time.

9. The method of claim 1 including obtaining data indicting a surface profile of the part under test for aiding in accurate positioning of a sensor.

10. The method of claim 1 including rotating or focusing on a selected ones of the first and second graphs simultaneously for aiding an operator in the evaluation of the material characteristics of the device under test.

11. The method of claim 1 wherein the step of detecting a single stream of diffracted energy includes detecting the diffraction or attenuation of the directed energy.

12. The method of claim 1 including selecting a point on a selected one of the first and second graphs, generating a report of the material characteristics for the point, and displaying the report along with the graphs to facilitate evaluation of the material characteristics at the point.

13. The method of claim 12 including selecting the characteristics from a group comprised of: stress, stress error, intensity ratio, average peak breadth, average full width at half maximum (FWHM), shear stress, stress tensor, error tensor, x-direction stress, y-direction stress, maximum shear, equivalent stress, hardness, grain size, dislocation density, plastic strain, percent plastic strain, percent cold work, phases, percent retained austenite, strain, strain error, shear strain, strain tensor, x-direction strain, y-direction strain, and maximum strain.

14. The method of claim 1 wherein directing energy includes scanning the selected portion of the part under test from different directions to obtain accurate measurements of the material characteristics.

15. The method of claim 1 wherein detecting the single stream of diffracted energy comprises detecting a single stream of raw diffracted energy having a single frequency.

16. The method of claim 1 further comprising identifying a potentially defective portion of the part under test based upon the visual comparison.

17. The method of claim 16 wherein the first material characteristic is stress and the second material characteristic is shear stress and wherein identifying a potentially defective portion of the part under test comprises determining that the part is potentially defective because the stress and shear stress are uniformly high in the same portion of the part under test as determined by the substantially simultaneous visual comparison of the first and second graphs.

18. The method of claim 16 wherein the first material characteristic is stress and the second material characteristic is error, and further comprising determining the intensity ratio and peak breadth from the single stream of diffracted energy, displaying the intensity ratio in a third graph and the peak breadth in a fourth graph, and wherein identifying a potentially defective portion of the part under test comprises determining that the part is potentially defective because the stress is high in a portion of the part under test and the error, intensity ratio, and peak breadth vary substantially in the same portion of the part under test as determined by the substantially simultaneous visual comparison of the first, second, third, and fourth graphs.

19. The method of claim 16 wherein the first material characteristic is stress and the second material characteristic is error, and further comprising determining the intensity ratio and peak breadth from the single stream of diffracted energy, displaying the intensity ratio in a third graph and the peak breadth in a fourth graph, and wherein identifying a potentially defective portion of the part under test comprises determining that the part is acceptable because the stress is high in a portion of the part under test and the error, intensity ratio, and peak breadth are low in the same portion of the part under test as determined by the substantially simultaneous visual comparison of the first, second, third, and fourth graphs.

20. The method of claim 16 wherein the first material characteristic is stress as measured at a first sensor and the second material characteristic is stress as measured at a second sensor and wherein identifying a potentially defective portion of the part under test comprises determining that the part is potentially defective because the stress as measured at the first sensor is substantially different from the stress as measured at the second sensor as determined by the substantially simultaneous visual comparison of the first and second graphs.

21. The method of claim 1 further comprising forming a third graph based upon a mathematical operation performed between the first and second graphs.

22. The method of claim 21 wherein forming a third graph comprises forming a third graph from a mathematical operation, the mathematical operation being a subtraction operation.

* * * * *

UNITED STATES PATENT AND TRADEMARK OFFICE
CERTIFICATE OF CORRECTION

| | | |
|---|---|---|
| PATENT NO. | : 7,265,754 B2 | Page 1 of 1 |
| APPLICATION NO. | : 10/706385 | |
| DATED | : September 4, 2007 | |
| INVENTOR(S) | : Michael Brauss | |

It is certified that error appears in the above-identified patent and that said Letters Patent is hereby corrected as shown below:

(Item 56) On Title Page
Page 1, Column 2, line 2, insert -- JR. -- after "Purcell" (Office Action dated November 1, 2005, page 2 List of references cited by examiner).

Column 25, line 60, delete "ones" and insert -- one -- therefor (from Amendment dated January 31, 2006, page 5, Claim 8, line 22).

Column 26, line 8, delete "ones" and insert -- one -- therefore (from Amendment dated January 31, 2006, page 6, Claim 11, line 9).

Signed and Sealed this

Twenty-fifth Day of March, 2008

JON W. DUDAS
*Director of the United States Patent and Trademark Office*